United States Patent
Jones et al.

(10) Patent No.: US 12,234,268 B2
(45) Date of Patent: Feb. 25, 2025

(54) RECOMBINANT HAGFISH PROTEINS AND FIBERS

(71) Applicants: Justin A. Jones, Nibley, UT (US); Randolph V. Lewis, Nibley, UT (US); Dong Chen, Logan, UT (US); Paula F. Oliveira, Logan, UT (US); Thomas Ian Harris, Logan, UT (US); Brianne Eileen Bell, Nibley, UT (US)

(72) Inventors: Justin A. Jones, Nibley, UT (US); Randolph V. Lewis, Nibley, UT (US); Dong Chen, Logan, UT (US); Paula F. Oliveira, Logan, UT (US); Thomas Ian Harris, Logan, UT (US); Brianne Eileen Bell, Nibley, UT (US)

(73) Assignee: UTAH STATE UNIVERSITY, North Logan, UT (US)

( * ) Notice: Subject to any disclaimer, the term of this patent is extended or adjusted under 35 U.S.C. 154(b) by 6 days.

(21) Appl. No.: 17/651,020

(22) Filed: Feb. 14, 2022

(65) Prior Publication Data

US 2022/0340622 A1    Oct. 27, 2022

Related U.S. Application Data

(60) Provisional application No. 63/174,742, filed on Apr. 14, 2021.

(51) Int. Cl.
*C07K 14/46* (2006.01)
*D01F 4/00* (2006.01)

(52) U.S. Cl.
CPC ............. *C07K 14/461* (2013.01); *D01F 4/00* (2013.01)

(58) Field of Classification Search
CPC ........... C07K 14/461; D01F 4/00; D01F 6/68; D01D 5/06
See application file for complete search history.

(56) References Cited

U.S. PATENT DOCUMENTS 6,852,691 B1 * 2/2005 Sukhatme .............. C07K 14/78
514/13.3
2019/0002529 A1 * 1/2019 Kogot ...................... C07K 1/14

OTHER PUBLICATIONS

Novagen pET System Manual/pET-19b vector; user manual publication date 2011 (Year: 2011).*
GenBank: HAL7885803.1 TPA: bifunctional DNA primase/helicase [*Escherichia coli*]; sequence publication date 2018 (Year: 2018).*
Bhattacharya et al., Impact of genetic variation on three dimensional structure and function of proteins, 2017, PLOS One, vol. 12, Issue 3, pp. 1-22 (Year: 2017) (Year: 2017).*
Fenton et al., Rheostat positions: A new classification of protein positions relevant to pharmacogenomics, 2020, Medicinal Chemistry Research, vol. 29, pp. 1133-1146 (Year: 2020) (Year: 2020).*
Guo et al., Protein tolerance to random amino acid change, 2004, PNAS, vol. 101, No. 25, pp. 9205-9210 (Year: 2004) (Year: 2004).*
UniProt, Q90501; Full=Thread biopolymer filament subunit alpha; Eptatretus stoutii (Pacific hagfish), 1998 (Year: 1998).*
UniProt, Q90502; Full=Thread biopolymer filament subunit gamma; Eptatretus stoutii (Pacific hagfish), 1998 (Year: 1998).*
Bhattacharya et al., Impact of genetic variation on three dimensional structure and function of proteins, 2017, PLOS One, vol. 12, Issue 3, pp. 1-22 (Year: 2017).*
Fenton et al., Rheostat positions: A new classification of protein positions relevant to pharmacogenomics, 2020, Medicinal Chemistry Research, vol. 29, pp. 1133-1146 (Year: 2020).*
Guo et al., Protein tolerance to random amino acid change, 2004, PNAS, vol. 101, No. 25, pp. 9205-9210 (Year: 2004).*
UniProt (with sequence alignment), Q90502; Full=Thread biopolymer filament subunit gamma; Eptatretus stoutii (Pacific hagfish), 1998 (Year: 1998).*

* cited by examiner

*Primary Examiner* — Jeffrey Stucker
*Assistant Examiner* — Brittney E Donoghue
(74) *Attorney, Agent, or Firm* — Ryan L. Marshall; Barnes & Thornburg LLP

(57) ABSTRACT

The present application provides fibers made from recombinant hagfish intermediate filament proteins. Methods of expressing and purifying the proteins, and methods of creating the fibers, are likewise disclosed. The method of purifying protein yields larger quantities of hagfish protein than have been previously achieved, and the fibers have the highest mechanical properties yet recorded for recombinant hagfish protein fibers.

7 Claims, 4 Drawing Sheets

Specification includes a Sequence Listing.

SEQUENCE LISTING

<160> NUMBER OF SEQ ID NOS: 7

<210> SEQ ID NO 1
<211> LENGTH: 674
<212> TYPE: PRT

<213> ORGANISM: Artificial Sequence
<220> FEATURE:
<223> OTHER INFORMATION: Recombinant HIFalpha

<400> SEQUENCE: 1

```
Met Gly His His His His His His His His Ser Ser Gly His
1               5                   10                  15

Ile Asp Asp Asp Asp Lys His Met His Asn Leu Asn Arg Phe Glu Met
            20                  25                  30

Ser Ile Ser Gln Thr Val Ser Lys Ser Tyr Thr Lys Ser Val Ser Arg
        35                  40                  45

Gly Gly Gln Gly Val Ser Tyr Ser Gln Ser Ser Ser His Lys Val Gly
50                  55                  60

Gly Gly Ser Val Arg Tyr Gly Thr Thr Tyr Ser Ser Gly Gly Ile Ser
65                  70                  75                  80

Arg Val Leu Gly Phe Gln Gly Gly Ala Gly Gly Ala Ala Ser Ala Gly
                85                  90                  95

Phe Gly Gly Ser Val Gly Gly Ser Gly Leu Ser Arg Val Leu Gly Gly
                100                 105                 110

Ser Met Val Ser Gly Tyr Arg Ser Gly Met Gly Val Gly Gly Leu Ser
            115                 120                 125

Leu Ser Gly Thr Ala Gly Leu Pro Val Ser Leu Arg Gly Val Gly Ala
            130                 135                 140

Gly Lys Ala Leu His Ala Ile Thr Ser Ala Phe Arg Thr Arg Val Gly
145                 150                 155                 160

Gly Pro Gly Thr Ser Val Gly Gly Tyr Gly Val Asn Tyr Ser Phe Leu
                165                 170                 175

Pro Ser Thr Ala Gly Pro Ser Phe Gly Gly Pro Phe Gly Gly Pro Phe
            180                 185                 190

Gly Gly Pro Phe Gly Gly Pro Leu Gly Pro Gly Tyr Ile Asp Pro Ala
            195                 200                 205

Thr Leu Pro Ser Pro Asp Thr Val Gln His Thr Arg Ile Arg Glu Lys
    210                 215                 220

Gln Asp Leu Gln Thr Leu Asn Thr Lys Phe Ala Asn Leu Val Asp Gln
225                 230                 235                 240

Val Arg Thr Leu Glu Gln His Asn Ala Ile Leu Lys Ala Gln Ile Ser
                245                 250                 255

Met Ile Thr Ser Pro Ser Asp Thr Pro Glu Gly Pro Val Asn Thr Ala
            260                 265                 270

Val Val Ala Ser Thr Val Thr Ala Thr Tyr Asn Ala Gln Ile Glu Asp
        275                 280                 285

Leu Arg Thr Thr Asn Thr Ala Leu His Ser Glu Ile Asp His Leu Thr
    290                 295                 300

Thr Ile Ile Asn Asp Ile Thr Thr Lys Tyr Glu Glu Gln Val Glu Val
305                 310                 315                 320

Thr Arg Thr Leu Glu Thr Asp Trp Asn Thr Lys Asp Asn Ile Asp
                325                 330                 335

Asn Thr Tyr Leu Thr Ile Val Asp Leu Gln Thr Lys Val Gln Gly Leu
            340                 345                 350

Asp Glu Gln Ile Asn Thr Thr Lys Gln Ile Tyr Asn Ala Arg Val Arg
        355                 360                 365

Glu Val Gln Ala Ala Val Thr Gly Gly Pro Thr Ala Ala Tyr Ser Ile
370                 375                 380

Arg Val Asp Asn Thr His Gln Ala Ile Asp Leu Thr Thr Ser Leu Gln
```

```
                385                 390                 395                 400
    Glu Met Lys Thr His Tyr Glu Val Leu Ala Thr Lys Ser Arg Glu Glu
                    405                 410                 415

Ala Phe Thr Gln Val Gln Pro Arg Ile Gln Glu Met Ala Val Thr Val
                    420                 425                 430

Gln Ala Gly Pro Gln Ala Ile Ile Gln Ala Lys Glu Gln Ile His Val
                    435                 440                 445

Phe Lys Leu Gln Ile Asp Ser Val His Arg Glu Ile Asp Arg Leu His
                    450                 455                 460

Arg Lys Asn Thr Asp Val Glu Arg Glu Ile Thr Val Ile Glu Thr Asn
    465                 470                 475                 480

Ile His Thr Gln Ser Asp Glu Trp Thr Asn Asn Ile Asn Ser Leu Lys
                    485                 490                 495

Val Asp Leu Glu Val Ile Lys Lys Gln Ile Thr Gln Tyr Ala Arg Asp
                    500                 505                 510

Tyr Gln Asp Leu Leu Ala Thr Lys Met Ser Leu Asp Val Glu Ile Ala
                    515                 520                 525

Ala Tyr Lys Lys Leu Leu Asp Ser Glu Glu Thr Arg Ile Ser His Gly
                    530                 535                 540

Gly Gly Ile Thr Ile Thr Thr Asn Ala Gly Thr Phe Pro Gly Gly Leu
    545                 550                 555                 560

Ser Ala Ala Pro Gly Gly Gly Ala Ser Tyr Ala Met Val Pro Ala Gly
                    565                 570                 575

Val Gly Gly Val Gly Leu Ala Gly Val Gly Tyr Gly Phe Arg Ser
                    580                 585                 590

Met Gly Gly Gly Gly Val Gly Tyr Gly Ala Gly Gly Gly Gly Val
                    595                 600                 605

Gly Tyr Gly Val Gly Gly Phe Gly Gly Met Gly Met Ser Met
                    610                 615                 620

Ser Arg Met Ser Met Gly Ala Ala Val Gly Gly Ser Tyr Gly Ser
    625                 630                 635                 640

Gly Ser Gly Tyr Ser Gly Gly Phe Gly Leu Ser Ser Arg Ala Gly
                    645                 650                 655

Tyr Ser Ala Ser Arg Lys Ser Tyr Ser Ser Ala Arg Ser Ser Arg
                    660                 665                 670

Ile Tyr

<210> SEQ ID NO 2
<211> LENGTH: 634
<212> TYPE: PRT
<213> ORGANISM: Artificial Sequence
<220> FEATURE:
<223> OTHER INFORMATION: Recombinant HIFgamma

<400> SEQUENCE: 2

Met Gly His His His His His His His His His Ser Ser Gly His
    1                   5                   10                  15

Ile Asp Asp Asp Asp Lys His Met His Asn Leu Asn Arg Phe Glu Met
                    20                  25                  30

Ala Ser His Ser Ser Val Ser Tyr Arg Ser Val Arg Thr Gly Gly Thr
                    35                  40                  45

Ser Ala Met Ile Gly Ser Ser Gly Tyr Gly Gly Ser Ser Ser Arg
                    50                  55                  60

Ala Met Gly Leu Gly Met Gly Ala Ala Gly Leu Ser Met Gly Gly Gly
    65                  70                  75                  80
```

```
Ser Phe Arg Val Gly Ser Ala Gly Ile Gly Gly Met Gly Ile Ser Ser
                85                  90                  95
Gly Ile Gly Gly Met Gly Ile Ser Ser Arg Ala Gly Gly Met Ser Ala
            100                 105                 110
Tyr Gly Ala Ala Ser Gly Gly Ala Gly Gly Phe Val Ser Gly Gly
            115                 120                 125
Val Pro Met Leu Gly Tyr Gly Gly Ala Gly Gly Phe Ile Gly Gly
            130                 135                 140
Val Ser Pro Gly Ile Met Ala Ser Pro Ala Phe Thr Ala Gly Arg Ala
145                 150                 155                 160
Ile Thr Ser Ala Gly Met Ser Gly Val Val Gly Thr Leu Gly Pro Ala
                165                 170                 175
Gly Gly Met Val Pro Ser Leu Val Ser Arg Asp Glu Val Lys Asn Ile
                180                 185                 190
Leu Gly Thr Leu Asn Gln Arg Leu Ala Ser Tyr Val Asp Lys Val Arg
                195                 200                 205
Gln Leu Thr Ile Glu Asn Glu Thr Met Glu Glu Leu Lys Asn Leu
            210                 215                 220
Thr Gly Gly Val Pro Met Ser Pro Asp Ser Thr Val Asn Leu Glu Asn
225                 230                 235                 240
Val Glu Thr Gln Val Thr Glu Met Leu Thr Glu Val Ser Asn Leu Thr
                245                 250                 255
Leu Glu Arg Val Arg Leu Glu Ile Asp Val Asp His Leu Arg Ala Thr
                260                 265                 270
Ala Asp Glu Ile Lys Ser Lys Tyr Glu Phe Glu Leu Gly Val Arg Met
            275                 280                 285
Gln Leu Glu Thr Asp Ile Ala Asn Met Lys Arg Asp Leu Glu Ala Ala
            290                 295                 300
Asn Asp Met Arg Val Asp Leu Asp Ser Lys Phe Asn Phe Leu Thr Glu
305                 310                 315                 320
Glu Leu Thr Phe Gln Arg Lys Thr Gln Met Glu Glu Leu Asn Thr Leu
                325                 330                 335
Lys Gln Gln Phe Gly Arg Leu Gly Pro Val Gln Thr Ser Val Ile Glu
            340                 345                 350
Leu Asp Asn Val Lys Ser Val Asn Leu Thr Asp Ala Leu Asn Val Met
            355                 360                 365
Arg Glu Glu Tyr Gln Gln Val Val Thr Lys Asn Val Gln Glu Ala Glu
            370                 375                 380
Thr Tyr Cys Lys Met Gln Ile Asp Gln Ile Gln Gly Ile Ser Thr Gln
385                 390                 395                 400
Thr Thr Glu Gln Ile Ser Ile Leu Asp Lys Glu Ile Asn Thr Leu Glu
                405                 410                 415
Lys Glu Leu Gln Pro Leu Asn Val Glu Tyr Gln Arg Leu Leu Thr Thr
            420                 425                 430
Tyr Gln Thr Leu Gly Asp Arg Leu Thr Asp Leu Gln Asn Arg Glu Ser
            435                 440                 445
Ile Asp Leu Val Gln Phe Gln Asn Thr Tyr Thr Arg Tyr Glu Gln Glu
450                 455                 460
Ile Glu Gly Asn Gln Val Asp Leu Gln Arg Gln Leu Val Thr Tyr Gln
465                 470                 475                 480
Gln Leu Leu Asp Val Lys Thr Ala Leu Asp Ala Glu Ile Ala Thr Tyr
                485                 490                 495
```

```
Lys Lys Leu Leu Glu Gly Gln Glu Leu Met Val Arg Thr Ala Met Ala
            500                 505                 510

Asp Asp Phe Ala His Ala Thr Val Val Arg Ser Gly Thr Leu Gly Gly
            515                 520                 525

Ala Ser Ser Ser Ser Val Gly Tyr Gly Ala Ser Ser Thr Thr Leu Gly
        530                 535                 540

Ala Ile Ser Gly Gly Tyr Ser Thr Gly Gly Ala Ser Tyr Ser Ala
545                 550                 555                 560

Gly Ala Gly Gly Ala Ser Tyr Ser Ala Gly Ala Gly Ala Ser Tyr
                565                 570                 575

Gly Val Gly Gly Gly Tyr Ser Gly Gly Ser Ser Ala Met Met Glu Gly
            580                 585                 590

Ser Ser Ser Gly Gly His Ser Met Tyr Ser Ser Ser Met Lys Arg
        595                 600                 605

Ser Ser Ser Lys Ser Ala Ser Ala Ser Ala Gly Gly Tyr Gly Thr Ser
        610                 615                 620

Gly His Asp Ser Thr Ile Ile Leu Gln Gln
625                 630
```

<210> SEQ ID NO 3
<211> LENGTH: 634
<212> TYPE: PRT
<213> ORGANISM: Artificial Sequence
<220> FEATURE:
<223> OTHER INFORMATION: Recombinant HIFgamma (C387S)

<400> SEQUENCE: 3

```
Met Gly His His His His His His His His Ser Ser Gly His
1               5                   10                  15

Ile Asp Asp Asp Asp Lys His Met His Asn Leu Asn Arg Phe Glu Met
            20                  25                  30

Ala Ser His Ser Ser Val Ser Tyr Arg Ser Val Arg Thr Gly Gly Thr
        35                  40                  45

Ser Ala Met Ile Gly Ser Ser Gly Tyr Gly Gly Ser Ser Ser Ser Arg
    50                  55                  60

Ala Met Gly Leu Gly Met Gly Ala Ala Gly Leu Ser Met Gly Gly Gly
65                  70                  75                  80

Ser Phe Arg Val Gly Ser Ala Gly Ile Gly Gly Met Gly Ile Ser Ser
                85                  90                  95

Gly Ile Gly Gly Met Gly Ile Ser Ser Arg Ala Gly Gly Met Ser Ala
            100                 105                 110

Tyr Gly Gly Ala Ala Ser Gly Gly Ala Gly Gly Phe Val Ser Gly Gly
        115                 120                 125

Val Pro Met Leu Gly Tyr Gly Gly Ala Gly Gly Phe Ile Gly Gly
    130                 135                 140

Val Ser Pro Gly Ile Met Ala Ser Pro Ala Phe Thr Ala Gly Arg Ala
145                 150                 155                 160

Ile Thr Ser Ala Gly Met Ser Gly Val Val Gly Thr Leu Gly Pro Ala
                165                 170                 175

Gly Gly Met Val Pro Ser Leu Val Ser Arg Asp Glu Val Lys Asn Ile
            180                 185                 190

Leu Gly Thr Leu Asn Gln Arg Leu Ala Ser Tyr Val Asp Lys Val Arg
        195                 200                 205

Gln Leu Thr Ile Glu Asn Glu Thr Met Glu Glu Leu Lys Asn Leu
    210                 215                 220
```

```
Thr Gly Gly Val Pro Met Ser Pro Asp Ser Thr Val Asn Leu Glu Asn
225                 230                 235                 240

Val Glu Thr Gln Val Thr Glu Met Leu Thr Glu Val Ser Asn Leu Thr
            245                 250                 255

Leu Glu Arg Val Arg Leu Glu Ile Asp Val Asp His Leu Arg Ala Thr
            260                 265                 270

Ala Asp Glu Ile Lys Ser Lys Tyr Glu Phe Glu Leu Gly Val Arg Met
        275                 280                 285

Gln Leu Glu Thr Asp Ile Ala Asn Met Lys Arg Asp Leu Glu Ala Ala
    290                 295                 300

Asn Asp Met Arg Val Asp Leu Asp Ser Lys Phe Asn Phe Leu Thr Glu
305                 310                 315                 320

Glu Leu Thr Phe Gln Arg Lys Thr Gln Met Glu Glu Leu Asn Thr Leu
                325                 330                 335

Lys Gln Gln Phe Gly Arg Leu Gly Pro Val Gln Thr Ser Val Ile Glu
            340                 345                 350

Leu Asp Asn Val Lys Ser Val Asn Leu Thr Asp Ala Leu Asn Val Met
        355                 360                 365

Arg Glu Glu Tyr Gln Gln Val Val Thr Lys Asn Val Gln Glu Ala Glu
370                 375                 380

Thr Tyr Ser Lys Met Gln Ile Asp Gln Ile Gln Gly Ile Ser Thr Gln
385                 390                 395                 400

Thr Thr Glu Gln Ile Ser Ile Leu Asp Lys Glu Ile Asn Thr Leu Glu
                405                 410                 415

Lys Glu Leu Gln Pro Leu Asn Val Glu Tyr Gln Arg Leu Leu Thr Thr
            420                 425                 430

Tyr Gln Thr Leu Gly Asp Arg Leu Thr Asp Leu Gln Asn Arg Glu Ser
        435                 440                 445

Ile Asp Leu Val Gln Phe Gln Asn Thr Tyr Thr Arg Tyr Glu Gln Glu
    450                 455                 460

Ile Glu Gly Asn Gln Val Asp Leu Gln Arg Gln Leu Val Thr Tyr Gln
465                 470                 475                 480

Gln Leu Leu Asp Val Lys Thr Ala Leu Asp Ala Glu Ile Ala Thr Tyr
                485                 490                 495

Lys Lys Leu Leu Glu Gly Gln Glu Leu Met Val Arg Thr Ala Met Ala
            500                 505                 510

Asp Asp Phe Ala His Ala Thr Val Val Arg Ser Gly Thr Leu Gly Gly
        515                 520                 525

Ala Ser Ser Ser Val Gly Tyr Gly Ala Ser Thr Thr Leu Gly
530                 535                 540

Ala Ile Ser Gly Gly Tyr Ser Thr Gly Gly Ala Ser Tyr Ser Ala
545                 550                 555                 560

Gly Ala Gly Gly Ala Ser Tyr Ser Ala Gly Ala Gly Ala Ser Tyr
                565                 570                 575

Gly Val Gly Gly Tyr Ser Gly Gly Ser Ser Ala Met Met Glu Gly
            580                 585                 590

Ser Ser Ser Gly Gly His Ser Met Tyr Ser Ser Ser Met Lys Arg
        595                 600                 605

Ser Ser Ser Lys Ser Ala Ser Ala Gly Gly Tyr Gly Thr Ser
    610                 615                 620

Gly His Asp Ser Thr Ile Ile Leu Gln Gln
625                 630
```

<210> SEQ ID NO 4
<211> LENGTH: 318
<212> TYPE: PRT
<213> ORGANISM: Artificial Sequence
<220> FEATURE:
<223> OTHER INFORMATION: Recombinant polypeptide of central rod domain of HIFalpha

<400> SEQUENCE: 4

```
Lys Gln Asp Leu Gln Thr Leu Asn Thr Lys Phe Ala Asn Leu Val Asp
 1               5                  10                  15

Gln Val Arg Thr Leu Glu Gln His Asn Ala Ile Leu Lys Ala Gln Ile
            20                  25                  30

Ser Met Ile Thr Ser Pro Ser Asp Thr Pro Glu Gly Pro Val Asn Thr
        35                  40                  45

Ala Val Val Ala Ser Thr Val Thr Ala Thr Tyr Asn Ala Gln Ile Glu
    50                  55                  60

Asp Leu Arg Thr Thr Asn Thr Ala Leu His Ser Glu Ile Asp His Leu
65                  70                  75                  80

Thr Thr Ile Ile Asn Asp Ile Thr Thr Lys Tyr Glu Glu Gln Val Glu
                85                  90                  95

Val Thr Arg Thr Leu Glu Thr Asp Trp Asn Thr Asn Lys Asp Asn Ile
            100                 105                 110

Asp Asn Thr Tyr Leu Thr Ile Val Asp Leu Gln Thr Lys Val Gln Gly
        115                 120                 125

Leu Asp Glu Gln Ile Asn Thr Thr Lys Gln Ile Tyr Asn Ala Arg Val
    130                 135                 140

Arg Glu Val Gln Ala Ala Val Thr Gly Gly Pro Thr Ala Ala Tyr Ser
145                 150                 155                 160

Ile Arg Val Asp Asn Thr His Gln Ala Ile Asp Leu Thr Thr Ser Leu
                165                 170                 175

Gln Glu Met Lys Thr His Tyr Glu Val Leu Ala Thr Lys Ser Arg Glu
            180                 185                 190

Glu Ala Phe Thr Gln Val Gln Pro Arg Ile Gln Glu Met Ala Val Thr
        195                 200                 205

Val Gln Ala Gly Pro Gln Ala Ile Ile Gln Ala Lys Glu Gln Ile His
    210                 215                 220

Val Phe Lys Leu Gln Ile Asp Ser Val His Arg Glu Ile Asp Arg Leu
225                 230                 235                 240

His Arg Lys Asn Thr Asp Val Glu Arg Glu Ile Thr Val Ile Glu Thr
                245                 250                 255

Asn Ile His Thr Gln Ser Asp Glu Trp Thr Asn Ile Asn Ser Leu
            260                 265                 270

Lys Val Asp Leu Glu Val Ile Lys Lys Gln Ile Thr Gln Tyr Ala Arg
        275                 280                 285

Asp Tyr Gln Asp Leu Leu Ala Thr Lys Met Ser Leu Asp Val Glu Ile
    290                 295                 300

Ala Ala Tyr Lys Lys Leu Leu Asp Ser Glu Glu Thr Arg Ile
305                 310                 315
```

<210> SEQ ID NO 5
<211> LENGTH: 318
<212> TYPE: PRT
<213> ORGANISM: Artificial Sequence
<220> FEATURE:
<223> OTHER INFORMATION: Recombinant polypeptide of central rod domain of HIFgamma

<400> SEQUENCE: 5

| Lys | Asn | Ile | Leu | Gly | Thr | Leu | Asn | Gln | Arg | Leu | Ala | Ser | Tyr | Val | Asp |
|---|---|---|---|---|---|---|---|---|---|---|---|---|---|---|---|
| 1 | | | | 5 | | | | | 10 | | | | | 15 | |

| Lys | Val | Arg | Gln | Leu | Thr | Ile | Glu | Asn | Glu | Thr | Met | Glu | Glu | Glu | Leu |
|---|---|---|---|---|---|---|---|---|---|---|---|---|---|---|---|
| | | | 20 | | | | | 25 | | | | | 30 | | |

| Lys | Asn | Leu | Thr | Gly | Gly | Val | Pro | Met | Ser | Pro | Asp | Ser | Thr | Val | Asn |
|---|---|---|---|---|---|---|---|---|---|---|---|---|---|---|---|
| | | | 35 | | | | | 40 | | | | | 45 | | |

| Leu | Glu | Asn | Val | Glu | Thr | Gln | Val | Thr | Glu | Met | Leu | Thr | Glu | Val | Ser |
|---|---|---|---|---|---|---|---|---|---|---|---|---|---|---|---|
| | 50 | | | | | 55 | | | | | 60 | | | | |

| Asn | Leu | Thr | Leu | Glu | Arg | Val | Arg | Leu | Glu | Ile | Asp | Val | Asp | His | Leu |
|---|---|---|---|---|---|---|---|---|---|---|---|---|---|---|---|
| 65 | | | | | 70 | | | | | 75 | | | | | 80 |

| Arg | Ala | Thr | Ala | Asp | Glu | Ile | Lys | Ser | Lys | Tyr | Glu | Phe | Glu | Leu | Gly |
|---|---|---|---|---|---|---|---|---|---|---|---|---|---|---|---|
| | | | | 85 | | | | | 90 | | | | | 95 | |

| Val | Arg | Met | Gln | Leu | Glu | Thr | Asp | Ile | Ala | Asn | Met | Lys | Arg | Asp | Leu |
|---|---|---|---|---|---|---|---|---|---|---|---|---|---|---|---|
| | | | 100 | | | | | 105 | | | | | 110 | | |

| Glu | Ala | Ala | Asn | Asp | Met | Arg | Val | Asp | Leu | Asp | Ser | Lys | Phe | Asn | Phe |
|---|---|---|---|---|---|---|---|---|---|---|---|---|---|---|---|
| | | | 115 | | | | | 120 | | | | | 125 | | |

| Leu | Thr | Glu | Glu | Leu | Thr | Phe | Gln | Arg | Lys | Thr | Gln | Met | Glu | Glu | Leu |
|---|---|---|---|---|---|---|---|---|---|---|---|---|---|---|---|
| | 130 | | | | | 135 | | | | | 140 | | | | |

| Asn | Thr | Leu | Lys | Gln | Gln | Phe | Gly | Arg | Leu | Gly | Pro | Val | Gln | Thr | Ser |
|---|---|---|---|---|---|---|---|---|---|---|---|---|---|---|---|
| 145 | | | | | 150 | | | | | 155 | | | | | 160 |

| Val | Ile | Glu | Leu | Asp | Asn | Val | Lys | Ser | Val | Asn | Leu | Thr | Asp | Ala | Leu |
|---|---|---|---|---|---|---|---|---|---|---|---|---|---|---|---|
| | | | | 165 | | | | | 170 | | | | | 175 | |

| Asn | Val | Met | Arg | Glu | Glu | Tyr | Gln | Gln | Val | Val | Thr | Lys | Asn | Val | Gln |
|---|---|---|---|---|---|---|---|---|---|---|---|---|---|---|---|
| | | | 180 | | | | | 185 | | | | | 190 | | |

| Glu | Ala | Glu | Thr | Tyr | Ser | Lys | Met | Gln | Ile | Asp | Gln | Ile | Gln | Gly | Ile |
|---|---|---|---|---|---|---|---|---|---|---|---|---|---|---|---|
| | | | 195 | | | | | 200 | | | | | 205 | | |

| Ser | Thr | Gln | Thr | Thr | Glu | Gln | Ile | Ser | Ile | Leu | Asp | Lys | Glu | Ile | Asn |
|---|---|---|---|---|---|---|---|---|---|---|---|---|---|---|---|
| | 210 | | | | | 215 | | | | | 220 | | | | |

| Thr | Leu | Glu | Lys | Glu | Leu | Gln | Pro | Leu | Asn | Val | Glu | Tyr | Gln | Arg | Leu |
|---|---|---|---|---|---|---|---|---|---|---|---|---|---|---|---|
| 225 | | | | | 230 | | | | | 235 | | | | | 240 |

| Leu | Thr | Thr | Tyr | Gln | Thr | Leu | Gly | Asp | Arg | Leu | Thr | Asp | Leu | Gln | Asn |
|---|---|---|---|---|---|---|---|---|---|---|---|---|---|---|---|
| | | | | 245 | | | | | 250 | | | | | 255 | |

| Arg | Glu | Ser | Ile | Asp | Leu | Val | Gln | Phe | Gln | Asn | Thr | Tyr | Thr | Arg | Tyr |
|---|---|---|---|---|---|---|---|---|---|---|---|---|---|---|---|
| | | | 260 | | | | | 265 | | | | | 270 | | |

| Glu | Gln | Glu | Ile | Glu | Gly | Asn | Gln | Val | Asp | Leu | Gln | Arg | Gln | Leu | Val |
|---|---|---|---|---|---|---|---|---|---|---|---|---|---|---|---|
| | | | 275 | | | | | 280 | | | | | 285 | | |

| Thr | Tyr | Gln | Gln | Leu | Leu | Asp | Val | Lys | Thr | Ala | Leu | Asp | Ala | Glu | Ile |
|---|---|---|---|---|---|---|---|---|---|---|---|---|---|---|---|
| | 290 | | | | | 295 | | | | | 300 | | | | |

| Ala | Thr | Tyr | Lys | Lys | Leu | Leu | Glu | Gly | Gln | Glu | Leu | Met | Val |
|---|---|---|---|---|---|---|---|---|---|---|---|---|---|
| 305 | | | | | 310 | | | | | 315 | | | |

<210> SEQ ID NO 6
<211> LENGTH: 2262
<212> TYPE: DNA
<213> ORGANISM: Artificial Sequence
<220> FEATURE:
<223> OTHER INFORMATION: Recombinant HIFalpha

<400> SEQUENCE: 6

```
gatctcaacc aagatgtcga tctcccaaac agtcagcaag agttacacca agagtgtcag    60
ccggggagga cagggtgtga gctacagcca aagttcctca cacaaagtcg gtggagggtc   120
ggttcgttat ggtacgactt actcaagcgg tgggatctcg agggtactgg gattccaagg   180
tggtgctgga ggagcagcga gtgctggttt tggcggatcg gttggtggat ccggtctttc   240
```

```
tcgagtactt gggggcagca tggtgagcgg ctacagatct ggaatgggag ttggtggcct    300
ctctctgtcc ggtacggcgg ggcttcctgt tagcttgcga ggtgtcggag caggaaaggc    360
cttgcacgcc atcacctctg ctttccgcac tcgtgttgga ggcccgggaa ccagcgttgg    420
aggatatggt gtcaattaca gcttcctgcc aagcactgct ggtccctcat ttggtggtcc    480
atttggtggt ccatttggtg gtccctttgg aggtcccctc ggaccaggtt acatcgaccc    540
agcaactcta ccatctcctg acacagtcca acacactcgc atccgggaga agcaggacct    600
gcaaaccctc aacaccaaat ttgctaatct ggtggatcag gtgcgtacat ggaacaaca     660
caacgccatc ctgaaagctc agatctccat gatcaccagc cccagtgaca ctccagaagg    720
ccctgtgaac acagcagtgg tgcaagcac agtgacggcg acctacaacg cacagatcga     780
agacctgagg accaccaaca cggcacttca ttctgagatt gatcacctga ccaccatcat    840
caacgacatt accaccaaat atgaagaaca agtggaagtg cacggacac tggagacaga     900
ctggaacaca aacaaagata atattgacaa cacctacttg accatcgtgg atctgcagac    960
aaaggtccag ggtttggatg aacagattaa caccaccaag cagatctaca atgcccgcgt   1020
ccgtgaggtg caggctgccg tcacaggtgg accaacagct gcctattcca tcagggtgga   1080
caacacccac caggctatag atctcaccac gtctttgcag gagatgaaga cccactacga   1140
ggttcttgcc acaaagagtc gtgaggaggc cttcacccag gttcagccaa ggatccaaga   1200
aatggccgtc accgtccagg ctggtcctca agctatcatc caggccaagg aacagataca   1260
cgtgttcaag ctccagatcg actcggttca ccgtgaaatt gatcgtctcc acaggaagaa   1320
cacagacgtg gagagagaga ttaccgtgat cgagacaaac atccacacac agtctgatga   1380
atggaccaac aacataaata gcctcaaggt ggacttagaa gtcattaaga agcaaatcac   1440
acagtatgcc agagactacc aagaccttct ggccaccaag atgtctctgg atgtggagat   1500
tgcagcttac aagaaactgc tggacagtga ggagaccaga ataagccatg gtggaggaat   1560
caccatcacc accaatgcag gaacattccc aggtggtcta tctgctgctc ctggtggtgg   1620
ggcttcatac gccatggttc ctgctggtgt tggaggagtc ggcctggctg agtcggtgg    1680
ttatggtttc aggagcatgg gaggaggtgg tggtgtggga tacggtgcag gaggtggtgg   1740
tgtaggatat ggtgttggtg gtggttttgg tggtgggatg ggaatgtcga tgagcaggat   1800
gtccatgggt gccgcggttg gaggaggcag ttacggttct ggttctggat actctggagg   1860
atttggactt cctccagcc gtgcaggtta cagcgccagc aggaaaagct acagttcagc   1920
tcgttcatca tcccggatct actgaggatt cttccaagat ttaaatagca aggacaatga   1980
cctcaatgtt ctcattagtt tggtgcataa atgaagttga tgatgatgat tgtaaattcc   2040
attcaagcat gaactttctt ttccttaatc tttactggaa ctaaaggcga atctccgctt   2100
gtgctgttga aaatgtcaaa ataatcactg aaatcgcatg atacgggaat tgttgaagaa   2160
tgctcatatt atgttgatta tatttgctgg aaaatgattt tactttgttg cttgtgtggg   2220
atttgccttt gcatgaaact cataaaacta ccacaattgc aa                      2262
```

<210> SEQ ID NO 7
<211> LENGTH: 2016
<212> TYPE: DNA
<213> ORGANISM: Artificial Sequence
<220> FEATURE:
<223> OTHER INFORMATION: Recombinant HIFgamma

<400> SEQUENCE: 7

-continued

```
ctgattgagc aaaaagcagc aatggcctct cactcatccg tcagctaccg ctctgtccgc      60
accggtggaa ccagcgccat gatcggctcc agtggctatg gaggctccag cagcagccgt    120
gcgatggggc ttggaatggg tgctgcaggc ttgtcaatgg ggggaggaag cttcagagtg    180
ggttctgcag ggataggagg tatgggcatt ccagtggga ttgggggtat gggaatttcc     240
agccgtgccg ggggatgtc tgcctatgga ggagctgcgt caggaggtgc tggaggcttt     300
gtcagtggtg gggtgccaat gctcggttat ggaggtggtg ctggtgggtt tattgggggt    360
gtaagccccg ggatcatggc aagcccagca tttactgcag gccgtgccat caccctcagca   420
ggtatgtcag gagtggttgg aacgctggga cctgcaggtg gaatggttcc ttcactggtg    480
agcagagatg aggtgaagaa catcttgggc accttgaacc agcgcttggc cagctatgta    540
gataaagtaa ggcagcttac aatcgagaat gagacaatgg aggaagaatt gaagaacctg    600
actggaggtg taccaatgtc tcctgactcg accgtgaatc tggagaatgt ggagacacaa    660
gtcaccgaaa tgctgacgga ggtttccaac ctgacgctgg aacgtgtacg tctggagatc    720
gacgtggacc atctgagagc cacagctgat gagatcaagt cgaagtacga gtttgagctt    780
ggtgtgagaa tgcaacttga aactgacatt gcaaacatga gagggacct tgaagccgca    840
aacgatatgc gcgttgacct agattcaaag tttaattttt tgactgagga gctgacattc    900
cagaggaaaa cacaaatgga ggaactgaac accctgaaac agcagtttgg cagacttgga   960
ccagtacaga catcagtgat tgaactggat aacgtgaagt ctgtcaacct taccgacgcc  1020
ctcaatgtga tgcgtgagga ataccagcag gtggtcacca gaacgtcca agaggctgag  1080
acgtattgca agatgcaaat tgatcagatc caaggaatct ccacccagac aactgagcag  1140
atttctattc tggacaaaga gattaatact ttggaaaaag agctgcaacc tctaaatgtg  1200
gaataccaga ggcttctgac cacgtaccaa accctgggag acagactgac agatttacag  1260
aacagggaga gcattgatct cgtccagttc caaaacacct acaccagata tgaacaggag  1320
atcgagggaa accaggtgga cctgcagagg caactggtga cttaccaaca gcttctggac  1380
gtgaagacgg ctctcgatgc tgaaatagcg acatacaaga agctcctcga gggacaagag  1440
ttaatggtaa ggacagccat ggctgatgac ttttgctcacg ctactgttgt cagaagtgga  1500
actcttggtg gagcttcctc aagtagtgta ggctatggtg ccagttcaac aacacttggt  1560
gccatttctg gaggctacag cacaggtgga ggagccagct acagtgcagg tgctggagga  1620
gcaagctaca gtgcaggtgc tggaggagca agctacggtg taggaggcgg ttatagtggt  1680
ggaagtagtg caatgatgga aggtagttcc tctggtggac acagcatgta cagcagcagc  1740
tctatgaaga gaagcagctc caagagtgcc agtgcatctg ctggtggtta cggaacaagc  1800
ggacatgaca gcaccatcat ccttcaacaa taaacgtgtc gctgccttt gacaacattt   1860
gtgaaacaac tttgagtcgt gacagccaca caagataaac cccgacatca cattcacaga  1920
tcattcattc actttcccac aattcagatg atgacaacaa tgtgagactt gacagttatc  1980
tgagtgcaaa caaataaaag tttcattgcc tggtaa                             2016
```

RECOMBINANT HAGFISH PROTEINS AND FIBERS

RELATED APPLICATION

This application claims priority to U.S. provisional application No. 63/174,742, filed Apr. 14, 2021. The disclosure of this priority application is incorporated herein in its entirety.

FEDERALLY-SPONSORED RESEARCH STATEMENT

This invention was made with government support under FA8075-14-D-0014, awarded by the United States Department of Defense. The government has certain rights in the invention.

SEQUENCE LISTING

This application contains a Sequence Listing, which has been submitted electronically in ASCII format and is hereby incorporated by reference in its entirety. The ASCII copy, created on Feb. 10, 2022, is named "Hagfish_350819" and is 28.0 bytes in size.

BACKGROUND

Hagfish are remarkable creatures, not only because of their unique anatomical features but, perhaps most interestingly, their unique adaptation to predation. Hagfish are capable of producing a slime that is reinforced by fibrous proteins. When the slime is expelled, it rapidly expands and can clog the gills of a predator, forcing them to release the hagfish. While the slime is of keen interest, the reinforcing fibers (intermediate filaments) are also exciting due to their remarkable mechanical properties. When these fibers are isolated from the slime matrix, draw-processed, and dried, they exhibit mechanical properties similar to those of natural dragline silk from orb-weaving spiders. The hagfish fibrous thread is heteropolymeric and composed of two proteins, with the two proteins denoted $\alpha$ and $\gamma$. These proteins share a common structural architecture: an $\alpha$-helical rod domain and N- and C-termini that are not as $\alpha$-helical. In the native fiber, these two proteins coil around each other in a classic coiled-coil conformation, and when these fibers are draw-processed the $\alpha$-helices convert to $\beta$-sheets.

Native hagfish intermediate filament fibers have been dissolved using formic acid and spun into fibers to understand fiber creation and development from spinning systems that are not mimetic to the natural system. While the mechanical properties of such fibers fell short of their naturally created counterparts, the study indicated the potential of these two proteins to assemble and form a fiber using alternative spinning technologies. This initial research led to attempts to generate the two proteins in *E. coli*, where the proteins were produced as full-length natural analogs. When the proteins were purified, the authors demonstrated that they would self-assemble at the surface of an electrolyte buffer in a native-like $\alpha$-helical conformation from which fibers could be pulled. Further, when the fibers were draw-processed, the hallmark $\alpha$-helix to $\beta$-sheet conversion was observed. Additional characterization with X-ray diffraction confirmed that the newly formed $\beta$-sheet crystallites were oriented along the axis of the fiber, creating the natural structural elements that can assist in providing strength to protein-based fibers. Again, the mechanical properties fell short of characterized natural fibers.

Hagfish intermediate filament proteins are much smaller (≈65 kDa) than the highly studied, and challenging to produce, spider silk proteins (>300 kDa). They also have a more even distribution of amino acids without the heavy reliance on glycine and alanine found in spider silk. This combination makes them a more amenable target for heterologous expression. Although there are two reports in the literature of recombinant expression of the two hagfish fibrous proteins, no attempts have been made at optimizing protein production and output using efficient bioreactors.

Recombinant production also allows the opportunity to study these two hagfish proteins individually and gain insight into their fiber-forming abilities, structures, and mechanical properties. There are intermediate filament proteins that are homopolymeric, with one of the most studied being vimentin. In one study, the recombinant form of human vimentin was produced in *E. coli*, purified, and then spun into fibers. When the vimentin filaments were allowed to self-assemble and then compacted, fibers were able to be pulled from the resulting gelatinous film and draw-processed. These vimentin fibers exhibited maximum tensile strengths of ~173 MPa.

BRIEF SUMMARY

A recombinant hagfish intermediate filament protein or a variant thereof is provided. The recombinant hagfish intermediate filament protein or a variant thereof comprises recombinant HIFα or recombinant HIFγ.

In some aspects, the recombinant hagfish intermediate filament protein or a variant thereof comprises recombinant HIFα.

In some aspects, the recombinant hagfish intermediate filament protein or a variant thereof is comprises recombinant HIFγ.

In some aspects, the recombinant HIFγ comprises a cysteine-to-serine mutation at position 387 (HIFγ$_{C387S}$).

In some aspects, the recombinant HIFα is SEQ ID NO: 1, SEQ ID NO: 4, or a variant thereof.

In some aspects, the recombinant HIFγ is SEQ ID NO: 2, SEQ ID NO: 3, SEQ ID NO: 5, or a variant thereof.

In some aspects, the recombinant HIFα comprises at least 85%, 90%, 95%, 99% or 100% sequence identity with SEQ ID NO: 1 or SEQ ID NO: 4.

In some aspects, the recombinant HIFγ comprises at least 85%, 90%, 95%, 99% or 100% sequence identity with SEQ ID NO: 2, SEQ ID NO: 3, or SEQ ID NO: 5.

In other aspects, a isolated or purified polynucleotide sequence encoding the recombinant hagfish intermediate filament protein or a variant thereof of claim 1.

In another aspect, a vector comprising the polynucleotide sequence encoding a recombinant hagfish intermediate filament protein or a variant thereof is provided herein.

In one aspect, the present disclosure provides a fiber including at least one recombinant hagfish intermediate filament protein, or a variant thereof. The recombinant hagfish intermediate filament protein may be HIFα, or HIFγ, or a variant of one of these. HIFγ may include a cysteine-to-serine mutation at position 387 (HIFγ$_{C387S}$). The protein component of the fiber may consist of HIFα; or may consist of HIFγ; or may consist of HIFγ$_{C387S}$. The fiber may instead include both HIFα and HIFγ, or variants thereof. In such an aspect, the ratio of HIFα to HIFγ may be about 10:1 to about 1:10. The ratio of HIFα to HIFγ may be about 9:1 to about 1:9, or about 8:1 to about 1:8, or about 7:1 to about 1:7, or about 6:1 to about 1:6, or about 5:1 to about 1:5, or about 4:1 to about 1:4, or about 3:1 to about 1:3, or about 2:1 to about 1:2. The ratio of HIFα to HIFγ may be about 1:1. At least one recombinant hagfish filament protein or variant thereof may be expressed in, and purified from, bacteria.

In another aspect, the present disclosure provides a method of making a fiber including at least one recombinant hagfish intermediate filament protein, or a variant thereof. The method may include expressing a recombinant hagfish intermediate filament protein, or a variant thereof, in a non-hagfish cell; purifying the recombinant hagfish intermediate filament protein or the variant thereof from the non-hagfish cell yielding purified protein; and spinning the fiber from the purified protein. The cell may be a bacterial cell, such as an *Escherichia coli* cell. The method may include drying the recombinant protein and dissolving in a solvent. The solvent may include 1,1,1,3,3,3-hexafluoro-2-propanol, formic acid, DMSO, and water.

In another aspect, the present disclosure provides a method of expressing and purifying a recombinant hagfish intermediate filament protein, or a variant thereof. The method may include expressing the fiber-forming protein, or the variant thereof, in non-hagfish cells, wherein expressing occurs in a bioreactor; and purifying the fiber-forming protein or the variant thereof from the non-hagfish cells to yield purified protein. The non-hagfish cells may be prokaryotic cells, such as *Escherichia coli* cells. The protein may be HIFα, or HIFγ, or HIFγ$_{(C387S)}$. The non-hagfish cells may be grown to an optical density at 600 nanometers ($OD_{600}$) of about 55 to about 120, or to an $OD_{600}$ of about 60 to about 100. The yield of the fiber-forming protein, or variant thereof, may be about 3 grams per liter to about 20 grams per liter, or about 5 grams per liter to about 15 grams per liter, or about 8 grams per liter. The protein may be purified from an inclusion body.

BRIEF DESCRIPTION OF THE DRAWINGS

Reference is made to the following drawings, wherein.

DETAILED DESCRIPTION

Figure 1:
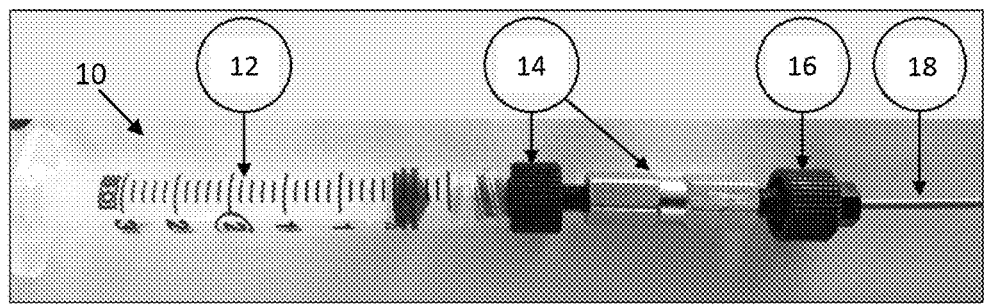
FIG. 1 illustrates a syringe extrusion device for use in accordance with an aspect of the present disclosure.

As used herein, the term "about," means "approximately but not necessarily equal to," and when used in the context of a numerical value or range set forth means a variation of ±15%, or less, of the numerical value. For example, a value differing by ±15%, ±12%, ±10%, or ±5%, among others, would satisfy the definition of "about."

An "expression vector" or "vector" is any genetic element, e.g., a plasmid, a mini-circle, a nanoplasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences.

As used herein, a "non-hagfish cell" is any cell from an organism other than one of the order Myxiniformes, including prokaryotic, eukaryotic, and archaeal cells.

As used herein, the term "variant," when used with reference to a protein, is a protein having an amino acid sequence that is at least about at least 75%, at least 80%, at least 85%, at least 90%, at least 91%, at least 92%, at least 93%, at least 94%, at least 95%, at least 96%, at least 97%, at least 98%, at least 99%, or 100% identical to the sequence of the referenced protein. The term "variant" also refers to a polypeptide that differs from the referenced polypeptide (for example, differing by at least one conservative amino acid substitution) but possesses the primary function of the referenced polypeptide.

The terms "identical" and its grammatical equivalents as used herein or "sequence identity" in the context of two nucleic acid sequences or amino acid sequences of polypeptides refer to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, Adv. Appl. Math., 2:482 (1981); by the alignment algorithm of Needleman and Wunsch, J. Mol. Biol., 48:443 (1970); by the search for similarity method of Pearson and Lipman, Proc. Nat. Acad. Sci U.S.A., 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, Gene, 73:237-244 (1988) and Higgins and Sharp, CABIOS, 5:151-153 (1989); Corpet et al., Nucleic Acids Res., 16:10881-10890 (1988); Huang et al., Computer Applications in the Biosciences, 8:155-165 (1992); and Pearson et al., Methods in Molecular Biology, 24:307-331 (1994). Alignment is also often performed by inspection and manual alignment. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, the percentage of residues in the smaller molecule finds a match residue in the larger molecule in accordance with the order by which the two molecules are optimally aligned.

By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand. It is generally appreciated that conditions can be rendered more stringent by the addition of increasing amounts of formamide.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free —NH$_2$ can be maintained. Exemplary conservative amino acid substitutions are shown in the following chart:

| Type of Amino Acid | Substitutable Amino Acids |
|---|---|
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The applicant undertook efforts to discover if the individual recombinant forms of the hagfish α and γ proteins would assemble into a fiber and to characterize their structural elements, mechanical properties, and the interplay between those features.

Applicant discovered that very high expression levels of recombinant hagfish intermediate filament (rHIF) proteins are obtainable in E. coli using small (~1 L) bioreactors. As a proof of concept, the process was scaled in E. coli to the 100 L bioreactor level, which demonstrated similarly high expression. An efficient purification procedure, which is both scalable and economical, is also reported. Finally, the fibers that are double draw-processed, from both the individual proteins and in a native-like 1:1 combination, were produced, and their resultant mechanical properties and the structural elements of the fibers are reported.

Expression Vector Construction

The genes encoding hagfish alpha and gamma proteins have been previously identified. One change was made in the natural gamma sequence. As is indicated, the cysteine that is ordinarily present in the natural hagfish gamma protein sequence was removed and replaced with serine. The removal of cysteine was an attempt to improve the purification of the proteins by removing the ability to form disulfide bonds. Provided that both proteins were expressed at high levels as inclusion bodies, this may not have been necessary. Finally, the pET-19k vector included a 10× histidine-tag at the N-terminal. While this tag was included, it was not utilized for purification. Rather, the histidine tag was used in western blot analysis to confirm the identity of the produced proteins. The recombinant proteins are denoted as recombinant hagfish intermediate filament alpha (rHIFα) or gamma (rHIFγ$_{(C387S)}$). The specific amino acid substitution denoted for rHIFγ$_{(C387S)}$ is identified as follows:

Recombinant HIFα as expressed: SEQ ID NO 1:
MGHHHHHHHHHHSSGHIDDDDKHMHNLNRFEMSISQTVSKSYTKSVSRGG

QGVSYSQSSSHKVGGGSVRYGTTYSSGGISRVLGFQGGAGGAASAGFGGS

VGGSGLSRVLGGSMVSGYRSGMGVGGLSLSGTAGLPVSLRGVGAGKALHA

ITSAFRTRVGGPGTSVGGYGVNYSFLPSTAGPSFGGPFGGPFGGPFGGPL

GPGYIDPATLPSPDTVQHTRIREKQDLQTLNTKFANLVDQVRTLEQHNAI

LKAQISMITSPSDTPEGPVNTAVVASTVTATYNAQIEDLRTTNTALHSEI

DHLTTIINDITTKYEEQVEVTRTLETDWNTNKDNIDNTYLTIVDLQTKVQ

GLDEQINTTKQIYNARVREVQAAVTGGPTAAYSIRVDNTHQAIDLTTSLQ

EMKTHYEVLATKSREEAFTQVQPRIQEMAVTVQAGPQAIIQAKEQIHVFK

LQIDSVHREIDRLHRKNTDVEREITVIETNIHTQSDEWTNNINSLKVDLE

VIKKQITQYARDYQDLLATKMSLDVEIAAYKKLLDSEETRISHGGGITIT

TNAGTFPGGLSAAPGGGASYAMVPAGVGGVGLAGVGGYGFRSMGGGGVG

YGAGGGGVGYGVGGGFGGGMGMSMSRMSMGAAVGGGSYGSGSGYSGGFGL

SSSRAGYSASRKSYSSARSSSRIY

Recombinant HIFγ as expressed: SEQ ID NO 2:
MGHHHHHHHHHHSSGHIDDDDKHMHNLNRFEMASHSSVSYRSVRTGGTSA
MIGSSGYGGSSSSRAMGLGMGAAGLSMGGGSFRVGSAGIGGMGISSGIGG
MGISSRAGGMSAYGGAASGGAGGFVSGGVPMLGYGGGAGGFIGGVSPGIM
ASPAFTAGRAITSAGMSGVVGTLGPAGGMVPSLVSRDEVKNILGTLNQRL
ASYVDKVRQLTIENETMEEELKNLTGGVPMSPDSTVNLENVETQVTEMLT
EVSNLTLERVRLEIDVDHLRATADEIKSKYEFELGVRMQLETDIANMKRD
LEAANDMRVDLDSKFNFLTEELTFQRKTQMEELNTLKQQFGRLGPVQTSV
IELDNVKSVNLTDALNVMREEYQQVVTKNVQEAETYCKMQIDQIQGISTQ
TTEQISILDKEINTLEKELQPLNVEYQRLLTTYQTLGDRLTDLQNRESID
LVQFQNTYTRYEQEIEGNQVDLQRQLVTYQQLLDVKTALDAEIATYKKLL
EGQELMVRTAMADDFAHATVVRSGTLGGASSSSVGYGASSTTLGAISGGY
STGGGASYSAGAGGASYSAGAGGASYGVGGGYSGGSSAMMEGSSSGGHSM
YSSSSMKRSSSKSASASAGGYGTSGHDSTIILQQ Recombinant HIFγ(C387S) as expressed:
SEQ ID NO 3:
MGHHHHHHHHHHSSGHIDDDDKHMHNLNRFEMASHSSVSYRSVRTGGTSA
MIGSSGYGGSSSSRAMGLGMGAAGLSMGGGSFRVGSAGIGGMGISSGIGG
MGISSRAGGMSAYGGAASGGAGGFVSGGVPMLGYGGGAGGFIGGVSPGIM
ASPAFTAGRAITSAGMSGVVGTLGPAGGMVPSLVSRDEVKNILGTLNQRL
ASYVDKVRQLTIENETMEEELKNLTGGVPMSPDSTVNLENVETQVTEMLT
EVSNLTLERVRLEIDVDHLRATADEIKSKYEFELGVRMQLETDIANMKRD
LEAANDMRVDLDSKFNFLTEELTFQRKTQMEELNTLKQQFGRLGPVQTSV
IELDNVKSVNLTDALNVMREEYQQVVTKNVQEAETYSKMQIDQIQGISTQ
TTEQISILDKEINTLEKELQPLNVEYQRLLTTYQTLGDRLTDLQNRESID
LVQFQNTYTRYEQEIEGNQVDLQRQLVTYQQLLDVKTALDAEIATYKKLL
EGQELMVRTAMADDFAHATVVRSGTLGGASSSSVGYGASSTTLGAISGGY
STGGGASYSAGAGGASYSAGAGGASYGVGGGYSGGSSAMMEGSSSGGHSM
YSSSSMKRSSSKSASASAGGYGTSGHDSTIILQQ In another aspect, the recombinant polypeptide may be the central rod domain of HIFα, SEQ ID NO: 4: KQDLQTLNTKFANLVDQVRTLEQHNAILKAQISMITSPSDTPEGPVNTAVVASTV TATYNAQIEDLRTTNTALHSEIDHLTTIINDITTKYEEQVEVTRTLETDWNTNKDN IDNTYLTIVDLQTKVQGLDEQINTTKQIYNARVREVQAAVTGGPTAAYSIRVDNT HQAIDLTTSLQEMKTHYEVLATKSREEAFTQVQPRIQEMAVTVQAGPQAIIQAKE QIHVFKLQIDSVHREIDRLHRKNTDVEREITVIETNIHTQSDEWTNNINSLKVDLE VIKKQITQYARDYQDLLATKMSLDVEIAAYKKLLDSEETRI, or a sequence 99% identical, 98% identical, 95% identical, 90% identical, 85% identical, 80% identical, or 75% identical thereto.

In another aspect, the recombinant polypeptide may be the central rod domain of HIFγ, SEQ ID NO: 5: KNILGTLNQRLASYVDKVRQLTIENETMEEELKNLTGGVPMSPDSTVNLENVET QVTEMLTEVSNLTLERVRLEIDVDHLRATADEIKSKYEFELGVRMQLETDIANM KRDLEAANDMRVDLDSKFNFLTEELTFQRKTQMEELNTLKQQFGRLGPVQTSVI ELDNVKSVNLTDALNVMREEYQQVVTKNVQEAETYSKMQIDQIQGISTQTTEQI SILDKEINTLEKELQPLNVEYQRLLTTYQTLGDRLTDLQNRESIDLVQFQNTYTRY EQEIEGNQVDLQRQLVTYQQLLDVKTALDAEIATYKKLLEGQELMV, or a sequence 99% identical, 98% identical, 95% identical, 90% identical, 85% identical, 80% identical, or 75% identical thereto. Such a sequence may optionally include the cysteine-to-serine mutation described herein.

In some aspects, the recombinant HIFα comprises SEQ ID NO: 1 or a variant thereof. In some aspects, the recombinant HIFα comprises SEQ ID NO: 4, or a variant thereof.

In some aspects, the recombinant HIFγ comprises SEQ ID NO: 2 or a variant thereof. In some aspects, the recombinant HIFγ comprises SEQ ID NO: 3 or a variant thereof. In some aspects, the recombinant HIFγ comprises SEQ ID NO: 5 or a variant thereof.

In some aspects, the HIFα comprises at least 85%, 90%, 95%, 99% or 100% sequence identity with SEQ ID NO: 1 or SEQ ID NO: 4.

In some aspects, the HIFγ comprises at least 85%, 90%, 95%, 99% or 100% sequence identity with SEQ ID NO: 2, SEQ ID NO: 3, or SEQ ID NO: 5.

It will be appreciated by a person of skill in the art that there are numerous amino acid sequences that can be included in a region of a recombinant protein, yielding a functional product. Affinity tags, such as the histidine tag disclosed herein, may be appended to the N-terminal region, the C-terminal region, or even in central portions of the amino acid sequences without impairing the structure or biological properties of a protein. Likewise, it will be appreciated that certain amino acid substitutions, insertions, and deletions can be made in the sequence of a polypeptide and yield a functional protein variant. This disclosure contemplates any and all uses of insertions, deletions, conservative amino acid substitutions, chimeras, affinity tags, linkers, or other amino acid sequences that could be incorporated into recombinant hagfish intermediate filament proteins which are do not occur in the wild type sequence but nonetheless allow for these proteins to be spun into filaments.

The full-length gene sequences were codon-optimized for expression in *E. coli* using ThermoFisher gene Optimizer™ software and were synthesized by ThermoFisher Scientific.

The pET19k cloning vector was generated by modifying the pET19b vector (Novagen) by replacing the ampicillin resistance gene with the kanamycin resistance gene from the pET26b vector (Novagen). Synthesized hagfish genes were inserted into the pET19k vector at the restriction sites of NdeI and BamHI. The resulting vectors were transformed into *E. coli* BL21 (DE3) chemically competent cells (New England Biolabs) to produce the two hagfish proteins.

A nucleic acid sequence useful for expressing recombinant hagfish intermediate filament alpha is as follows (SEQ ID NO: 6):

```
  1  gatctcaacc aagatgtcga tctcccaaac agtcagcaag
     agttacacca agagtgtcag
 61  ccggggagga cagggtgtga gctacagcca aagttcctca
     cacaaagtcg gtggagggtc
```

```
121  ggttcgttat ggtacgactt actcaagcgg tgggatctcg
     agggtactgg gattccaagg
181  tggtgctgga ggagcagcga gtgctggttt tggcggatcg
     gttggtggat ccggtctttc
241  tcgagtactt gggggcagca tggtgagcgg ctacagatct
     ggaatgggag ttggtggcct
301  ctctctgtcc ggtacggcgg ggcttcctgt tagcttgcga
     ggtgtcggag caggaaaggc
361  cttgcacgcc atcacctctg ctttccgcac tcgtgttgga
     ggcccgggaa ccagcgttgg
421  aggatatggt gtcaattaca gcttcctgcc aagcactgct
     ggtccctcat ttggtggtcc
481  atttggtggt ccatttggtg gtccctttgg aggtcccctc
     ggaccaggtt acatcgaccc
541  agcaactcta ccatctcctg acacagtcca acacactcgc
     atccgggaga agcaggacct
601  gcaaaccctc aacaccaaat ttgctaatct ggtggatcag
     gtgcgtacat tggaacaaca
661  caacgccatc ctgaaagctc agatctccat gatcaccagc
     cccagtgaca ctccagaagg
721  ccctgtgaac acagcagtgg tggcaagcac agtgacggcg
     acctacaacg cacagatcga
781  agacctgagg accaccaaca cggcacttca ttctgagatt
     gatcacctga ccaccatcat
841  caacgacatt accaccaaat atgaagaaca agtggaagtg
     acacggacac tggagacaga
901  ctggaacaca aacaaagata atattgacaa cacctacttg
     accatcgtgg atctgcagac
961  aaaggtccag ggtttggatg aacagattaa caccaccaag
     cagatctaca atgcccgcgt
1021 ccgtgaggtg caggctgccg tcacaggtgg accaacagct
     gcctattcca tcagggtgga
1081 caacccac caggctatag atctcaccac gtctttgcag
     gagatgaaga cccactacga
1141 ggttcttgcc acaaagagtc gtgaggaggc cttcacccag
     gttcagccaa ggatccaaga
1201 aatggccgtc accgtccagg ctggtcctca agctatcatc
     caggccaagg aacagataca
1261 cgtgttcaag ctccagatcg actcggttca ccgtgaaatt
     gatcgtctcc acaggaagaa
1321 cacagacgtg gagagagaga ttaccgtgat cgagacaaac
     atccacacac agtctgatga
1381 atggaccaac aacataaata gcctcaaggt ggacttagaa
     gtcattaaga agcaaatcac
1441 acagtatgcc agagactacc aagaccttct ggccaccaag
     atgtctctgg atgtggagat
1501 tgcagcttac aagaaactgc tggacagtga ggagaccaga
     ataagccatg gtggaggaat
1561 caccatcacc accaatgcag gaacattccc aggtggtcta
     tctgctgctc ctggtggtgg
1621 ggcttcatac gccatggttc ctgctggtgt tggaggagtc
     ggcctggctg gagtcggtgg
1681 ttatggtttc aggagcatgg gaggaggtgg tggtgtggga
     tacggtgcag gaggtggtgg
1741 tgtaggatat ggtgttggtg gtggttttgg tggtgggatg
     ggaatgtcga tgagcaggat
1801 gtccatgggt gccgcggttg gaggaggcag ttacggttct
     ggttctggat actctggagg
1861 atttggactt tcctccagcc gtgcaggtta cagcgccagc
     aggaaaagct acagttcagc
1921 tcgttcatca tcccggatct actgaggatt cttccaagat
     ttaaatagca aggacaatga
1981 cctcaatgtt ctcattagtt tggtgcataa atgaagttga
     tgatgatgat tgtaaattcc
2041 attcaagcat gaactttctt ttccttaatc tttactggaa
     ctaaaggcga atctccgctt
2101 gtgctgttga aaatgtcaaa ataatcactg aaatcgcatg
     atacgggaat tgttgaagaa
2161 tgctcatatt atgttgatta tatttgctgg aaaatgattt
     tactttgttg cttgtgtggg
2221 atttgccttt gcatgaaact cataaaacta ccacaattgc
     aa
```

In some aspects, the nucleic acid sequence useful for expressing recombinant hagfish intermediate filament alpha is SEQ ID NO: 6 or a sequence that binds to a complementary sequence of SEQ ID NO: 6 under high stringency conditions.

A nucleic acid sequence useful for expressing recombinant hagfish intermediate filament gamma is as follows (SEQ ID NO: 7):

```
1    ctgattgagc aaaaagcagc aatggcctct cactcatccg
     tcagctaccg ctctgtccgc
```

-continued

```
  61 accggtggaa ccagcgccat gatcggctcc agtggctatg
     gaggctccag cagcagccgt
 121 gcgatggggc ttggaatggg tgctgcaggc ttgtcaatgg
     ggggaggaag cttcagagtg
 181 ggttctgcag ggataggagg tatgggcatt ccagtgggga
     ttgggggtat gggaatttcc
 241 agccgtgccg ggggatgtc tgcctatgga ggagctgcgt
     caggaggtgc tggaggcttt
 301 gtcagtggtg gggtgccaat gctcggttat ggaggtggtg
     ctggtgggtt tattgggggt
 361 gtaagccccg ggatcatggc aagcccagca tttactgcag
     gccgtgccat cacctcagca
 421 ggtatgtcag gagtggttgg aacgctggga cctgcaggtg
     gaatggttcc ttcactggtg
 481 agcagagatg aggtgaagaa catcttgggc accttgaacc
     agcgcttggc cagctatgta
 541 gataaagtaa ggcagcttac aatcgagaat gagacaatgg
     aggaagaatt gaagaacctg
 601 actggaggtg taccaatgtc tcctgactcg accgtgaatc
     tggagaatgt ggagacacaa
 661 gtcaccgaaa tgctgacgga ggtttccaac ctgacgctgg
     aacgtgtacg tctggagatc
 721 gacgtggacc atctgagagc cacagctgat gagatcaagt
     cgaagtacga gtttgagctt
 781 ggtgtgagaa tgcaacttga aactgacatt gcaaacatga
     agagggacct tgaagccgca
 841 aacgatatgc gcgttgacct agattcaaag tttaattttt
     tgactgagga gctgacattc
 901 cagaggaaaa cacaaatgga ggaactgaac accctgaaac
     agcagtttgg cagacttgga
 961 ccagtacaga catcagtgat tgaactggat aacgtgaagt
     ctgtcaacct taccgacgcc
1021 ctcaatgtga tgcgtgagga ataccagcag gtggtcacca
     agaacgtcca agaggctgag
1081 acgtattgca agatgcaaat tgatcagatc caaggaatct
     ccacccagac aactgagcag
1141 atttctattc tggacaaaga gattaatact ttggaaaaag
     agctgcaacc tctaaatgtg
1201 gaataccaga ggcttctgac cacgtaccaa accctgggag
     acagactgac agatttacag
1261 aacagggaga gcattgatct cgtccagttc caaaacacct
     acaccagata tgaacaggag
1321 atcgagggaa accaggtgga cctgcagagg caactggtga
     cttaccaaca gcttctggac
1381 gtgaagacgg ctctcgatgc tgaaatagcg acatacaaga
     agctcctcga gggacaagag
1441 ttaatggtaa ggacagccat ggctgatgac tttgctcacg
     ctactgttgt cagaagtgga
1501 actcttggtg gagcttcctc aagtagtgta ggctatggtg
     ccagttcaac aacacttggt
1561 gccatttctg gaggctacag cacaggtgga ggagccagct
     acagtgcagg tgctggagga
1621 gcaagctaca gtgcaggtgc tggaggagca agctacggtg
     taggaggcgg ttatagtggt
1681 ggaagtagtg caatgatgga aggtagttcc tctggtggac
     acagcatgta cagcagcagc
1741 tctatgaaga gaagcagctc caagagtgcc agtgcatctg
     ctggtggtta cggaacaagc
1801 ggacatgaca gcaccatcat ccttcaacaa taaacgtgtc
     gctgccttt gacaacattt
1861 gtgaaacaac tttgagtcgt gacagccaca caagataaac
     cccgacatca cattcacaga
1921 tcattcattc actttcccac aattcagatg atgacaacaa
     tgtgagactt gacagttatc
1981 tgagtgcaaa caaataaaag tttcattgcc tggtaa
```

In some aspects, the nucleic acid sequence useful for expressing recombinant hagfish intermediate filament alpha is SEQ ID NO: 7 or a sequence that binds to a complementary sequence of SEQ ID NO: 7 under high stringency conditions.

In some aspects, a vector comprises SEQ ID NO: 6 or a sequence that binds to a complementary sequence of SEQ ID NO: 6 under high stringency conditions.

In some aspects, a vector comprises SEQ ID NO: 7 or a sequence that binds to a complementary sequence of SEQ ID NO: 7 under high stringency conditions.

Recombinant Hagfish rHIFα and rHIFγ$_{(C387S)}$ Protein Expression

Before scaling to the BioFlo610 (~100 L) level of production, protein expression was validated first in shaker flasks (data not shown) and in New Brunswick Scientific BioFlo 115 (~1 L) bioreactors. Both rHIFα and rHIFγ$_{(C387S)}$ were expressed as inclusion bodies at all scales. Each construct was produced in triplicate using the BioFlo115 bioreactors. From each batch, the protein was purified, lyophilized, and weighed. The protocols, to scale-up from the BioFlo115 to BioFlo610 bioreactors, remained the same in terms of instrument operation, media formulation, and feeds given that all of the reported fed-batch fermentations were conducted with New Brunswick bioreactors using the BioCommand software. As such, the protocol and media components are reported only once. In one run, the entire cell mass from the BioFlo610 runs was not able to be purified at one time, as was performed with the BioFlo115 runs, due to the relatively large cell masses (19 kg for rHIFα and 13 kg for rHIFγ$_{(C387S)}$) and equipment limitations. Instead, multiple purifications were performed on the total cell mass from each run. The protein yield was then averaged across those purifications.

The rHIFα and rHIFγ$_{(C387S)}$ protein expressions were scaled-up in a New Brunswick Scientific BioFlo610 bioreactor. The first seed solution was grown in 100 mL of LB medium plus 10 g/L glucose and 100 mg/L kanamycin in 500 mL Erlenmeyer flasks with rotary shaking (220 rpm) at 37° C. to an OD$_{600}$ of one. The first seed solution was then inoculated into 3 L of LB with 10 g/L glucose and 100 mg/L kanamycin in a 10 L bottle to produce the second seed solution. The second seed solution was grown with rotary shaking (130 rpm) at 30° C. to an OD$_{600}$ of one. Inoculum culture was pumped into the BioFlo610 fermenter with 50-70 L of sterilized modified K12 medium (Table 1), 100 mg/L kanamycin, and 0.02% v/v C-8840 antifoam (New London Chemical).

TABLE 1

Medium for protein production

Initial Medium:

| | |
|---|---|
| Potassium phosphate monobasic anhydrous | 2 g L$^{-1}$ |
| Potassium phosphate dibasic trihydrate | 4 g L$^{-1}$ |
| Ammonium phosphate dibasic anhydrous | 5 g L$^{-1}$ |
| Yeast Extract | 5 g L$^{-1}$ |
| Tryptone | 2.5 g L$^{-1}$ |
| Added after autoclaving of the initial medium: | |
| Glucose | 25 g L$^{-1}$ |
| Magnesium sulfate heptahydrate | 0.5 g L$^{-1}$ |
| Thiamine | 2.5 mg L$^{-1}$ |
| X1000 trace metal solution | 1 mL L$^{-1}$ |
| Glucose feeding solution: | |
| Glucose | 500 g L$^{-1}$ |
| Tryptone | 10 g L$^{-1}$ |
| Magnesium sulfate heptahydrate | 10 g L$^{-1}$ |
| Thiamine | 40 mg L$^{-1}$ |
| X1000 trace metal | 1 mL L$^{-1}$ |
| [χ1000] trace metal solution in water: | |
| Sodium chloride | 25 g L$^{-1}$ |
| Zinc sulfate heptahydrate | 5 g L$^{-1}$ |
| Manganese chloride tetrahydrate | 20 g L$^{-1}$ |
| Ferric chloride hexahydrate | 23.8 g L$^{-1}$ |
| Cupric sulfate pentahydrate | 2 g L$^{-1}$ |
| Boric acid | 2.9 g L$^{-1}$ |
| Sodium molybdate dihydrate | 2.5 g L$^{-1}$ |
| 6N sulfuric acid | 62.5 mL L$^{-1}$ |

Starting fermentation temperature was set at 37° C. and the pH setpoint was 6.8, which was regulated by the automatic addition of 20% ammonium hydroxide throughout the fermentation. A dissolved O$_2$ level of 80% was cascade controlled by agitation (150-400 rpm), gas flow (10-100 SLPM), and bubbling air and O2 (0-100%) into the culture. Glucose feeding solution (24-28 L) was fed during the fermentation controlled by the BioCommand software. The glucose level was monitored by a ReliOn Prime Blood Glucose Monitoring System (Walmart). Induction of protein expression was initiated when an OD$_{600}$ value of 55-60 was obtained. The target proteins, rHIFα or rHIFγ$_{(C387S)}$, were induced with 1 mM isopropyl β-d-1-thiogalactopyranoside (IPTG) at 28° C. After 4 hours of induction, when the OD$_{600}$ value was around 100, the culture was harvested by centrifugation for 15 minutes at 8000-10,000 rcf at 4° C., and the cell pellets were stored in a –80° C. freezer until processed for purification.

Protein Purification and Verification

The frozen hagfish rHIFα and rHIFγ$_{(C387S)}$ cell pellets were thawed and resuspended at 10 mL/g of cells in lysis buffer (50 mM Tris and 200 mM NaCl at pH 7.9 (rHIFα) or pH 5.5 (rHIFγ$_{(C387S)}$) with 200 μg/mL lysozyme. The solutions were sonicated for 10 cycles of 10 seconds, with intervals of 45 seconds between cycles with a VCX 1500 (Sonics Vibracell).

Lysate was centrifuged at 10,000 rcf for 15 minutes at 4° C., the resulting pellets (hagfish rHIFα and rHIFγ$_{(C387S)}$ inclusion bodies) were resuspended in wash buffer 1 (100 mM Tris, 5 mM ethylenediaminetetraacetic acid (EDTA), 0.5 M urea, 2% v/v Triton X-100, and 5 mM dithiothreitol (DTT); pH 7.9 for rHIFα and pH 5.5 for rHIFγ$_{(C387S)}$) at 5 mL/g cells. After centrifugation, the pellets were rewashed with wash buffer 1 and followed by two washes of wash buffer 2 (100 mM Tris, 5 mM EDTA, and 5 mM DTT; pH 7.9 for rHIFα and pH 5.5 for rHIFγ$_{(C387S)}$) at 5 mL/g cells all with centrifugation parameters described above. The pellets were then washed with 1:1 1×TAE:isopropyl alcohol (IPA) (1×TAE: 40 mM Tris, 1 mM EDTA, and 20 mM acetic acid). A final set of washes of 1:1 deionized water:IPA was then performed until the conductivity of the supernatant was <20 μS/cm. The washed protein was then lyophilized. Production yields were determined by weighing the recovered dry protein and comparing it to either the cell mass or the final working volume in the bioreactor to give grams of protein recovered per kilogram of cell mass (g/kg) or grams of protein recovered per liter of media (g/L).

The purified proteins were mixed 1:1 v/v with 2× Laemmli Sample Buffer (Bio-Rad) and heat-treated at 100° C. for 5 minutes before loading on polyacrylamide gels (Novex 4-20% Tris-Glycine from ThermoFisher). A dual-color protein standard (Bio-Rad) was included on all gels. The gels were allowed to run for 60 minutes at a constant 110 V. After SDS-PAGE analysis, the gels were rinsed using deionized water before being stained with 5 mL Bio-Rad Bio-Safe Coomassie Stain for 60 minutes. The gel was then destained using deionized water for 60 minutes.

The protein samples separated by SDS-PAGE were transferred to a PVDF/Immobilon™-P Membrane (Millipore) by electroblotting using the Mini Trans-Blot System (Bio-Rad). Blots were set up as specified by the manufacturer (Bio-Rad). All transfers were performed under a constant 200 mA for 50 minutes. After fixing of the proteins, the membranes were subjected to immunoblotting analyses using 1×TBS-T (1×TBS-T: 20 mM Tris, 140 mM sodium chloride, and 0.05% v/v Tween-20, pH 7.4) and Carnation dehydrated milk as the blocking reagents at a concentration of 5% w/v. The primary antibody was an anti-6× his epitope tag, (mouse) antibody (Rockland) at a 1:5000 dilution, and the secondary was an anti-mouse IgG (H+L) AP conjugate antibody (Promega) at a 1:10,000 dilution. Each addition of antibody was allowed to mix on the membranes for 30 minutes, with 15 minute rinses of TBS-T in between each antibody and before the development addition. For the detection of alkaline phosphatase activity on the PVDF membrane, 1-Step™ NBT/BCIP Substrate Solution (ThermoFisher) was used as specified by the manufacturer.

A method of making a fiber of is provided. The method includes expressing a recombinant hagfish intermediate filament protein, or a variant thereof, in a non-hagfish cell; purifying the recombinant hagfish intermediate filament protein or the variant thereof from the non-hagfish cell yielding purified protein; and spinning the fiber from the purified protein.

In some aspects, the non-hagfish cell is *E. coli*.

In some aspects, the method yields about 5 grams per liter to about 10 grams per liter of recombinant hagfish intermediate filament protein.

In some aspects, purifying the recombinant hagfish intermediate filament protein comprises processing inclusion bodies.

In some aspects, the method further includes drying the purified protein to yield dried protein.

In some aspects, the dried protein is dissolved in a solvent.

In some aspects, the solvent is selected from: 1,1,1,3,3,3-hexafluoro-2-propanol, formic acid, DMSO, water, and combinations thereof.

In some aspects, the solvent comprises 1,1,1,3,3,3-hexafluoro-2-propanol.

In some aspects, spinning the fiber comprises dispensing the fiber in a coagulation bath.

In some aspects, the coagulation bath comprises an alcohol.

In some aspects, spinning the fiber comprises dispensing the fiber in a stretch bath.

In some aspects, spinning the fiber comprises dispensing the fiber in more than one stretch bath.

In some aspects each stretch bath comprises an alcohol and water.

In some aspects, a stretch bath comprises Mg and Ca ions. In some aspects, the stretch bath comprises about 100 to about 700 mg/L of calcium ion. In some aspects, the stretch bath comprises about 300 to about 500 mg/L of calcium ion. In some aspects, the stretch bath comprises about 400 mg/L of calcium ion. In some aspects, the stretch bath comprises about 1000 mg/L to about 1500 mg/L of magnesium ion. In some aspects, the stretch bath comprises about 1200 mg/L to about 1500 mg/L of magnesium ion. In some aspects, the stretch bath comprises about 1300 mg/L of magnesium ion. In some aspects, the stretch bath comprises about 1320 mg/L of magnesium ion.

In some aspects, spinning the fiber comprises stretching a nascent fiber to up to double its length in a stretch bath.

In some aspects, a nascent fiber is not stretched while dispensed in a stretch bath.

In some aspects, the method further includes drying the fiber.

A method of isolating a fiber-forming protein or a variant thereof is provided. The method includes expressing the fiber-forming protein, or the variant thereof, in non-hagfish cells, wherein expressing occurs in a bioreactor; and purifying the fiber-forming protein or the variant thereof from the non-hagfish cells to yield purified protein.

In some aspects, the non-hagfish cells are prokaryotic cells.

In some aspects, the prokaryotic cells comprise *Escherichia coli* cells.

In some aspects, the protein comprises recombinant HIFα.

In some aspects, the protein comprises recombinant HIFγ.

In some aspects, the protein comprises of HIFγ$_{(C387S)}$.

In some aspects, the non-hagfish cells are grown to an optical density at 600 nanometers (OD$_{600}$) of about 55 to about 120. In some aspects, the non-hagfish cells are grown to an OD$_{600}$ of about 60 to about 100.

In some aspects, a yield of the fiber-forming protein, or variant thereof, is about 3 grams per liter to about 20 grams per liter.

In some aspects, the yield of the fiber-forming protein or the variant thereof is about 5 grams per liter to about 15 grams per liter.

In some aspects, the yield of the fiber-forming protein or the variant thereof is about 8 grams per liter.

Example 1: Detailed Protein Purification Protocol

The following protocol provides detailed steps for purifying hagfish intermediate filament proteins. Portions of this protocol may be employed in concert with, or as an alternative to, the procedures disclosed elsewhere in this document. All equipment choices, reagent suppliers and identities, and so forth, can be altered as seen fit by one of skill in the art.

Terminology: TFF stands for tangential flow filtration and involves hundreds of porous hollow fibers enclosed in a large column that is attached to a pump and pressure gauges via tubing and tubing connectors. "Column" is used in place of "TFF column" throughout the protocol. Feed refers to the inlet of the pump and is what goes into the top of the TFF column. Retentate refers to what is retained by the filters and is placed back into the solution being filtered. Retained particulates are larger than the cut off pore size for the specific column. The retentate line is where back pressure is applied to ensure that the columns fill and to aid in the filtering process. Permeate refers to the fluid that permeates out of the TFF column. Permeated particulates are smaller than the cut off pore size for the specific column. 0.45 um column has a pore size of 0.45 um while 0.65 um column has a pore size of 0.65 um. 0.65 um column (Repligen: K02-E65U-07-S); 0.45 um column (Cytiva: CFP-4-E-9). Lysate is the solution of lysed cells; lysate tank is often used to refer to the lysate solution.

Main Purification Method: Prepare Lysis Buffer with 80-100 L total volume. Lysis Buffer: 1 mM Tris (ultra-pure grade, Amresco: 0497-50KG), 200 mM NaCl (Morton pure and natural water softener crystals). The solution was pH-ed to isoelectric point of the protein being purified using concentrated hydrochloric acid (ACS reagent grade, 37%; Pharmco-Aaper: 28400ACS). For alpha, pH 7.9. For gamma, pH 5.5.

Per 1 kg of frozen cell mass; 1 g lysozyme (Scott Laboratories: Lysovin) was mixed in to 2-3 L lysis buffer. Ideally, a hammer is used to break cell mass into smaller chunks. A drill was used with a mixer attachment to mix the buffer, cell mass, and lysozyme. Lysing solution was placed on a magnetic stir plate overnight in a 4° C. cold room for continued mixing. A Sonics Vibracell VCX1500 was used to sonicate the full volume (roughly 3-4 L total) for 10 cycles of 10 seconds active sonication and 45 seconds resting in between the active sessions. While sonicating, a magnetic stir bar and stir plate were used to keep the solution mixing for better exposure. This can be done in smaller batches when necessary (i.e. bucket doesn't fit on stir plate and underneath the sonicator). If the cells did not appear to breaking apart, additional lysozyme was mixed in and more aggressive mixing with the drill or an immersion blender was also used.

To prepare the columns: columns were rinsed both with warm tap water and with a small amount of back pressure applied (approximately 1 psi in and out) to ensure the columns are able to completely fill. 0.65 um column: Total flow was at roughly 8 L/min with pressure set to 0.5-1 psi in and out. 0.45 um column: Total flow was at roughly 5 L/min with pressure set to 0.5-1 psi in and out. Ideally, all out flowing hoses were placed into an empty bucket while the feed hoses are in the warm tap water. For carefully cared for columns, 8-15 L of water was sent through the columns before the outflow was clear and the next phase of rinsing occurred. All the hoses were placed in the water bucket and allowed to run at the same settings as described above in this paragraph until the buffer was ready or a minimum of 5 minutes had passed. The columns were primed using the prepared lysis buffer and same speed settings for a minimum of 5 minutes or until ready to process the cell mass.

Columns were set up such that the feed and retentate lines of both columns are located in the lysate bucket (lysed cell mass in lysis buffer) while the permeate lines of both columns were in a clean and empty waste stream bucket. For ease of tracking the visual appearance of the permeate fluid and sample taking, place the permeate lines in their own small containers that can overflow into the larger container.

A level control system was set up by placing the Low-level sensors (controls TFF pumps) at 6-8 L and the High-level sensor (controls the Buffer Feed pump) at 12-15 L. These were secured to a pipe that was also secured in place along the wall of the bucket. SpectraPure: LLC-PH-115; low level controls were from reversing the switch in the control box to turn off when the volume was too low, high levels were used without modification. If the lysed solution was particularly viscous, all the level control trip points were raised or repeat sonication. The Buffer Feed pump outflow line was placed into the lysate tank and the inlet into the lysis buffer tank. Dial speed was set at 4; this was only on when the lysate volume falls below the sensor's trip point set in the previous step.

The lysate solution was diluted to 10-12 L using the lysis buffer. If desired, the lysate solution was mixed once more with the drill and mixer attachment. An initial sample of the lysate solution was taken (LT-0 is common ID used, along with date and protein type). When taking lysate tank samples, the solution was diluted 1:2 in lysis buffer. The process began by turning the pumps on and using the following settings: 0.65 um Column: Transmembrane pressure (TMP) at 4-6 psi, retentate flow rate around 8 L/min, and flux rate around 5.5-10 LMH; 0.45 um Column: Transmembrane pressure (TMP) at 4-5 psi, retentate flow rate around 5 L/min, and flux rate around 7-10 LMH.

i. $TMP = \left(\dfrac{P_{Feed} + P_{Retentate}}{2}\right) - P_{Permeate}$ ii. $\text{flux} = \dfrac{\text{permeate flow rate}\left(\dfrac{L}{\text{hour}}\right)}{\text{Surface Area}\,(m^2)}$ Periodically during the process, samples were collected from the permeate lines to monitor purification progress. This served as a fail safe to check for unexpected protein passage through the column(s) due to column failure. The lysate tank went through this constant volume diafiltration until at least one of the criteria are met: 5-8 hours of run time or permeate fluids were clear and not discolored or 80-100 L of lysis buffer had passed through the columns. Upon meeting at least one of these criteria, the lysate tank was concentrated down to 12 L, from its diafiltration volume of 15 L. This was achieved by turning off the buffer feed pump and removing the lines from the feed tank and lysate tank.

If desired, the Alternative Method can begin now, that process is described after the Main Method.

Once concentrated, the columns were flushed with 4 L of TFF Wash Buffer 1. It was best to flush the columns individually rather than together. Ideal flush: retentate line to an empty beaker, feed line in the buffer, and the permeate line in the waste container; run the pump until 1 L of solution had flowed from retentate line or until the flow from the retentate was mostly clear. The retentate fluid was then added to the lysate fluid with the remaining wash buffer 1 volume. The solution was then left to sit overnight at room temperature (19-22° C.). TFF Wash Buffer 1: 0.025M Tris, 10 mM EDTA disodium salt dihydrate (VWR: 0105-12KG), 1M urea (DudaDiesel: Urea45), 1% Triton X-100 (RPI: 400001); pH to isoelectric point (5.5 gamma, 7.9 alpha). Columns were then be placed in 8-10 L of warm tap water and allowed to rinse for a minimum of 10 minutes using the same settings described in the column preparation description above. If time permitted, the columns were placed in cleaning solution, at 4 L per column. If not, the pumps were shut off and the valves closed to keep the columns soaking in water overnight. Further processing of the lysate was then diverged into two different methods, depending on chemical availability, starting cell mass size (if smaller than 1 kg), and centrifuge availability and capabilities.

The Protein was washed on the TFF (Common Method). The filtration process resumed using the same settings of the previous lysate column step with the exception of not reconnecting the lysis buffer feed pump. The lysate volume was allowed to reduce back to 12 L then another 4 L of TFF Wash Buffer 1 was added. When the lysate volume again reached 12 L, 4 L of TFF Wash Buffer 2 was added. TFF Wash Buffer 2: 32 mM Tris, 8 mM EDTA disodium salt dihydrate, 0.16M Acetic Acid. When the lysate volume reaches 12 L, add the final 4 L of TFF Wash Buffer 2. The lysis buffer feed pump was set up so that the inlet was in a barrel (60-80 L) of deionized water and turned on. The lysate and water set up was allowed to run until either: conductivity of the permeate fluid was below 200 μS/cm or conductivity of the permeate fluid was relatively stable. The permeate fluid was clear and water-like in appearance at that point.

The final concentration process was performed by turning off the water feed pump and removing its hoses from the water and lysate tanks. The lysate was allowed to concentrate until: the final volume approached 4 L (initial volume used in preparing the cell mass) or pressure readings began to increase, indicating the solution was too viscous to proceed.

All pumps were turned off and an equal amount of 99% Isopranol was added (IPA; Pharmco: 231000099) to the lysate. The lysate/IPA solution was then centrifuged at 13,704 rcf for 45 minutes at 4-5° C. The resulting supernatant was removed and discarded while the pellet was removed and placed in a beaker with all the pellet collections from the run. Sometimes the solution did not pellet completely from overwhelming the centrifuge bottle with too much protein in too little volume. This was often evident by either a cloudy but similarly colored supernatant layer just above the pellet or by a pool of protein sitting on the bottom of the bottle.

For maximum recovery, the cloudy layer and/or protein pool was poured into the pellet collection bucket for further processing. A minimum of 4 L of 50% IPA was added (1:1 IPA:deionized water) to the protein pellet container. If there was a lot of other liquid already present, an equal amount of 99% IPA was added to that liquid first. It was best to add enough of the 50% IPA to have an immersion blender be fully covered and for the pellet to be fully mixed together. After that, the remaining 50% IPA was added. It was ideal to cover the protein solution with plastic wrap and let it sit overnight in a 4° C. cold room. Mixing on a stir plate was optional; the protein did sometimes settle. The protein solution was centrifuged at 13,704 rcf for a minimum of 45 minutes at 4-5° C. and the IPA wash was repeated until the conductivity of the supernatant was below 200 µS/cm.

Pellet was collected in pre-weighed storage containers and frozen. Typically, a 1 kg cell mass purification fit in two 500 mL sample bottles. Once fully frozen, the bottle's lid was removed and replaced with three layers of tissue paper that were kept in place with a rubber band around the bottle's opening and lyophilized.

Dry protein was placed in a coffee grinder (Bodum) capable of ultrafine or espresso level coarseness. It was best to set the coarseness to medium, process the full amount of protein, then adjust to ultrafine coarseness and place the protein back into the grinder for final processing. The final protein was weighed.

Alternative Method (begins after the lysate diafiltration step). The final concentration process was performed by turning off the buffer feed pump and removing the buffer feed hoses. The lysate was allowed to concentrate until: final volume approached 4 L (initial volume used in preparing the cell mass) or pressure readings began to increase, indicative of the solution was too viscous to proceed.

About 300 mL of 50×TAE solution was added to the lysate and stirred. 50×TAE: 2M Tris, 0.05M EDTA disodium salt dihydrate, 1M Acetic acid. Concentrated lysate was centrifuged at 13,704 rcf for 45 minutes at 4-5° C.; poured off, and disposed of the supernatant while collecting the pellet in a beaker. About 2 L of Centrifuge Wash Buffer 1 was added to the pellet container and blended using an immersion blender. It was best to add enough solution to submerge the immersion blender and then using the remainder of the 2 L to rinse off the blender. Centrifuge Wash Buffer 1: 100 mM Tris, 5 mM EDTA, 0.5M Urea, 2% Triton X-100, 5 mM DTT; pH-ed to isoelectric point with concentrated hydrochloric acid. The steps were repeated until a total of 4 L of Centrifuge Wash Buffer 1 was used. Supernatant was disposed and the pellet was collected as before but the protein was then washed with Centrifuge Wash Buffer 2. Centrifuge Wash Buffer 2: 100 mM Tris, 5 mM EDTA, 5 mM DTT pH-ed to isoelectric point with concentrated hydrochloric acid.

The pellet was collected and blended in 3 L of 1×TAE 50% IPA, using an immersion blender. 40 mL 50×TAE per liter of total volume mixed with 50% IPA. Example: 3 L total volume: 60 mL 50×TAE, 1440 mL deionized water, 1500 mL 99% IPA. The pellet was blended with a minimum 2 L of 50% IPA, using an immersion blender, and then centrifuged at the same settings. The preceding step was repeated with new 50% IPA until the supernatant conductivity was below 200 µS/cm. It was best to have the protein soak in either the 1×TAE 50% IPA or plain 50% IPA solution over one night to allow for optimal cleaning. The pellet was collected in pre-weighed storage containers and frozen. Typically, a 1 kg cell mass purification fit in two 500 mL sample bottles. Once fully frozen, the bottle's lid was removed and replaced with three layers of tissue paper that were kept in place with a rubber band around the bottle's opening and the protein was lyophilized. Dry protein was placed in a coffee grinder (Bodum) capable of ultrafine or espresso level coarseness. It was best to set the coarseness to medium, process the full amount of protein, then adjust to ultrafine coarseness and place the protein back into the grinder for final processing.

Fiber Preparation and Production

The dried proteins were dissolved in 1,1,1,3,3,3-Hexafluoro-2-propanol (HFIP) (Oakwood Chemical) at a concentration of 5% w/v. HFIP was not previously explored as a solvent from which to spin hagfish intermediate filament fibers, but may play a role in driving α-helical conformations in proteins, recreating the natural structures of these proteins. Our findings demonstrate that HFIP can aid in producing superior fiber mechanical properties to determine the functional capacity of proteins in question.

Supporting this assertion is a recent study that utilized HFIP as a solvent to generate native-like mechanical properties of spider dragline silk from a full-length analog of MaSp1 (one of the two proteins that comprise dragline silk) for the first time. Smaller fragments of MaSp1 were expressed and then the full-length analog was assembled using the intein system. Rather, HFIP is capable of producing fibers that mimic the mechanical properties of natural fibers.

The two protein types were weighed out into a 4 mL capacity glass vial (Wheaton) for a 2 mL dope of 5% weight-to-volume (w/v) concentration, and then 2 mL of HFIP were added, the vial was then capped, and sealed with Parafilm. Additionally, a combination dope was made by mixing equal amounts of both, rHIFα and rHIFγ$_{(C387S)}$ proteins in an overall 5% w/v protein concentration in 2 mL of HFIP. The dopes were designated by their protein content as rHIFα, 1:1 rHIFα:rHIFγ$_{(C387S)}$ or 1:1 combination, and rHIFγ$_{(C387S)}$. For a formic acid dope, utilizing a single port, the concentration of rHIFα may be 20% w/v, and the concentration of rHIFγ$_{(C387S)}$ may be 15%, for an overall 15% w/v protein concentration. For a formic acid dope, utilizing multiple ports, the concentration of rHIFα may be 20% w/v, and the concentration of rHIFγ$_{(C387S)}$ may be 15%, for an overall 10% w/v protein concentration.

Protein dope solutions were allowed to solvate for 7 days. They were then centrifuged at 18,000 rcf for 10 minutes to remove any remaining particulates. FIG. 1 illustrates a syringe extrusion device 10 which was used in the following procedure. The supernatant was loaded into a BD 3 mL syringe 12 of the extrusion device 10. A spinning port 14 was placed onto the luer-lok end of the syringe. This was accomplished using polyether ether ketone (PEEK) tubing adapters 16 for connecting PEEK tubing 18 to the syringe. In this instance, the PEEK tubing 18 had an internal diameter of 0.254 millimeters.

Figure 2:
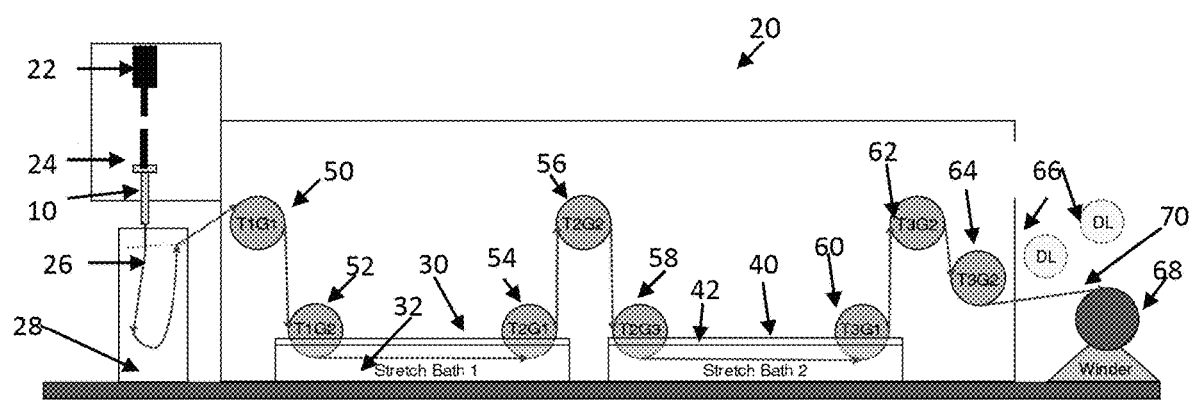
FIG. 2 provides a schematic view of a fiber extrusion and spinning apparatus for use in accordance with an aspect of the present disclosure.

The loaded syringe system 10 was placed into a custom extrusion spinning machine 20, as has been previously described, such as by Copeland et al. in ACS Biomater. Sci. Eng. 1 (7) (2015) 577-584, and as seen in FIG. 2. The machine 20 includes a plunger press 22 in operable contact with and for actuating syringe system 10, which is held in place by syringe holder 24. The syringe system 10 extrudes its contents into coagulation bath 28, to form nascent fiber 26. The nascent fiber 26 is a looped over a series of first spools 50 and 52 and into first stretch bath 30, which contains first stretch liquid 32. After stretching, the nascent fiber 26 loops over second spools 54, 56, and 58 and into second stretch bath 40, which contains second stretch liquid 42. The nascent fiber 26 is stretched a second time and moves over third spools 60, 62, and 64, past drying lamps 66, and onto spool 68, where finished fiber 70 is wound.

The bath contents were: coagulation bath 28 at 99% isopropyl alcohol (IPA), the first stretch bath 30 having first stretch liquid 32 at 80% IPA:20% ultra-pure water, and the second stretch bath 40 having second stretch solution at 20% IPA:80% ultra-pure water. The as-spun fibers were only extruded into the coagulation bath without being threaded through the spinning instrument. The stretches are reported as 1×1×, 1.5×1.5×, and 2×2×. For example, the 2×2× stretch denotes that the fiber was draw-processed to 2× the initial length in the first stretch bath (80% IPA) and then drawn again to 2× the length in the second stretch bath (20% IPA) for a total of 600% draw-processed. The 1×1× stretch denotes that no deliberate stretch was applied in either bath. The fiber was simply pulled from the coagulation bath, threaded through the instrument, and collected on the winding spool. To promote drying and prevent fibers from sticking together or to the collecting spool 68, drying lamps 66 were utilized for each spin between the final godet and the spool. Three stretch factors were investigated for this study: 1×1× (0% draw-processed), 1.5×1.5× (375% draw-processed), and 2×2× (600% draw-processed) and applied to all three protein formulations (rHIFα, 1:1 rHIFα:rHIFγ$_{(C387S)}$, and rHIFγ-$_{(C387S)}$)

Fiber Mechanical Analysis

Fibers were allowed to dry overnight on the collection spools at 24° C. and 16% humidity. Individual fiber samples were then mounted across a rectangular 19 mm opening on plastic film C-shaped cards, as has been previously reported by Albertson et al. in J. Mech. Behav. Biomed. Mater. 29 (2014) 225-234. Tape and cyanoacrylate were used to secure the fibers to cards to prevent slipping during measuring and testing. A Motic BA310 microscope coupled with the Motic Image Plus 2.0 program was then used to measure fiber diameters at nine different points along with the 19 mm long fiber segments. A MTS Synergie 100 tensile testing instrument with a custom 10 g load cell (Transducer Techniques), was used to perform the uniaxial tensile test on the fibers at an extension rate of 5 mm/min and an acquisition rate of 120 Hz. Sample sizes of twenty to twenty-five individual fibers were tested for every protein and stretch factor combination. The extension and load data were then exported to Microsoft Excel. The raw data in Microsoft Excel, along with average fiber diameter measurements, were used to calculate the ultimate tensile strength, strain, toughness, and elastic modulus for each fiber.

Fiber Structural Analysis

The collected fiber samples were also probed with Fourier-transform infrared (FTIR) spectroscopy to evaluate the compositions of secondary protein structures present. As-spun fibers were gently scooped out of the coagulation bath and allowed to dry in a similar fashion as the stretched fibers prior to analysis. A minimum of at least 50 individual fibers were obtained from the collection spools for each unique combination of protein (rHIFα, 1:1 rHIFα:rHIFγ$_{(C387S)}$, and rHIFγ$_{(C387S)}$) and stretch factor (1×1×, 1.5×1.5×, and 2×2×). The individual fibers were then twisted together to form a multi-fiber bundle that was used for the spectroscopic analysis. A Varian 660-IR instrument (Agilent) fitted with horizontal MIRacle single reflection attenuated total reflectance module (Pike Technologies) was used to obtain the FTIR spectra. Measurements were obtained for each bundle by wrapping it upon itself, into a small coil, and then securely clamping it directly onto the crystal stage. The collection was performed with Resolution Pro software over the spectral range of 600 cm$^{-1}$ to 4000 cm$^{-1}$, with 32 scans, a resolution of 4 cm$^{-1}$, and an aperture setting of 4 cm$^{-1}$ at 4000 cm$^{-1}$. Background scans were collected before each bundle with the exact conditions that were used for the bundle. Spectral correction and deconvolution for secondary structure quantification was performed at the Amide I region (1600 cm$^{-1}$ to 1700 cm$^{-1}$) using OriginPro and a similar method as previously described by Boni and colleagues (ACS Appl. Mater. Interfaces. 10 (47) (2018) 40460-40473.) The only variation to the described method was the use of Gaussian curves for peak fitting. All secondary structure peak assignments were based upon previous assignments used for the characterization of fibrous proteins (see Hu et al., Macromolecules. 39 (18) (2006) 6161-6170; and Guo et al., Biomacromolecules. 19 (3) (2018) 906-917).

Statistical Analysis

All values presented are provided in mean±standard deviation format. Analyses were first performed using a two-factor ANOVA to determine if any statistically significant differences were present. The specific significant differences were then determined with a Tukey post hoc analysis test. A p-value of <0.05 was considered statistically significant.

3. Results

Production and Recovery of rHIF Proteins

Both proteins were successfully synthesized at high levels at a laboratory scale (BioFlo115 at ~1 L). At the BioFlo115 level of production, both rHIFα and rHIFγ$_{(C387S)}$ proteins were produced and recovered on average at ≥45 g/kg cell mass (≥8 g/L, Table 2). There was some variability between runs as shown below. In one trial, rHIFα was induced for 5 hours for two runs rather than the standard 4 hour induction used for the others. This was an attempt to drive protein expression higher for rHIFα, which was successful. No manipulations were made to the induction time for rHIFγ$_{(C387S)}$.

TABLE 2

| | BioFlo115 protein yields | | | |
|---|---|---|---|---|
| Run # | Recovered Protein (g) | Volumetric Yield (g L$^{-1}$) | Mass Yield (g kg$^{-1}$) | Induction Time (h) |
| | rHIFα | | | |
| 1 | 8 | 6.7 | 37.2 | 4 |
| 2 | 10 | 8.3 | 46.5 | 5 |
| 3 | 12 | 10.0 | 55.8 | 5 |
| Average | 10 ± 2.0 | 8.3 ± 1.7 | 46.5 ± 9.3 | 4.7 |
| | rHIFγ$_{(C387S)}$ | | | |
| 1 | 12 | 10.0 | 55.8 | 4 |
| 2 | 9 | 7.5 | 41.9 | 4 |
| 3 | 8 | 6.7 | 37.2 | 4 |
| Average | 9.7 ± 2.1 | 8.1 ± 1.7 | 45.0 ± 9.7 | 4 |

All BioFlo115 runs were ≈1.2 L final volume.

When production of the two proteins was scaled to the BioFlo610 bioreactor (~100 L) the production yields remained relatively consistent from those observed in the BioFlo115 bioreactors (~1 L). The production and subsequent recovery of the two proteins resulted in a mass yield of 39 g/kg cell mass (7.8 g/L) for rHIFα and 45 g/kg cell mass (8.5 g/L) for rHIFγ$_{(C387S)}$ (Table 3).

TABLE 3

Protein production yields

| Purification # | Cell Mass (g) | Volume Equivalent (L) | Recovered Protein (g) | Volumetric Yield (g L$^{-1}$) | Mass Yield (g kg$^{-1}$) |
|---|---|---|---|---|---|
| rHIFα | | | | | |
| 1 | 400 | 2 | 17 | 8.5 | 42.5 |
| 2 | 400 | 2 | 13 | 6.5 | 32.5 |
| 3 | 400 | 2 | 14 | 7 | 35 |
| 4 | 400 | 2 | 15 | 7.5 | 37.5 |
| 5 | 400 | 2 | 18 | 9 | 45 |
| 6 | 400 | 2 | 16 | 8 | 40 |
| Average | 400 | 2 | 15.5 ± 1.9 | 7.8 ± 0.9 | 38.8 ± 4.7 |
| rHIFγ$_{(C387S)}$ | | | | | |
| 1 | 400 | 2.1 | 15 | 7.1 | 37.5 |
| 2 | 400 | 2.1 | 19 | 9 | 47.5 |
| 3 | 400 | 2.1 | 20 | 9.5 | 50 |
| 4 | 400 | 2.1 | 17 | 8.1 | 42.5 |
| 5 | 500 | 2.5 | 23 | 9 | 46 |
| Average | 420 ± 45 | 2.2 ± 0.2 | 18.8± | 8.5 ± 1.0 | 44.7 ± 4.9 |

Final BioFl0610 volumes were 95 L and 68 L and 19 kg and 13 kg for rHIFα and rHIFγ$_{(C387S)}$, respectively.

In one trial, while the BioFlo115 bioreactors were run in triplicate for each construct to validate protein production, the BioFlo610 (~100 L) bioreactor was only run once for each construct. Since both rHIFα and rHIFγ$_{(C387S)}$ were expressed as inclusion bodies, no attempts were made to quantify the protein in the soluble fraction.

Figure 3:
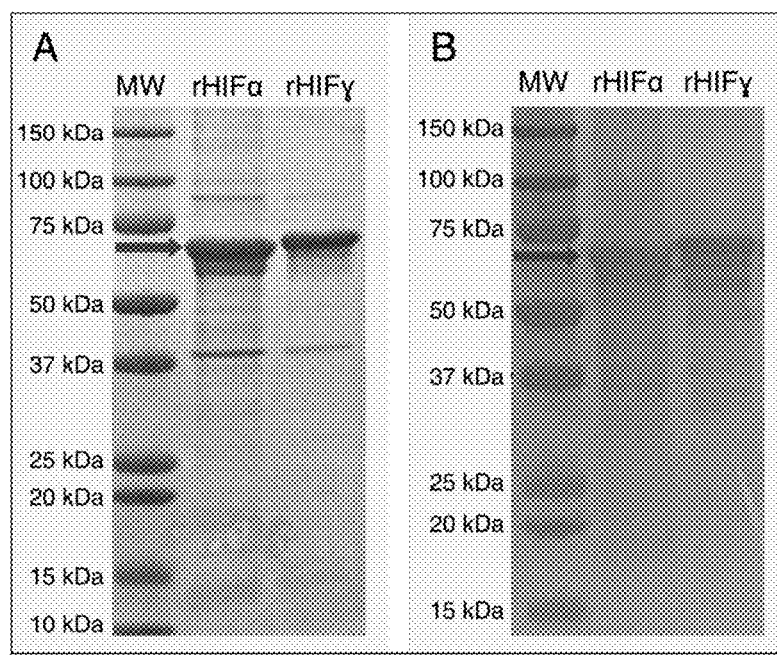
FIG. 3 is (A) a Coomassie-stained protein gel and (B) a Western blot using an anti-histidine tag affinity reagent of purified rHIFα and rHIFγ$_{(C387S)}$.

As shown in FIG. 3, both proteins were purified to a high degree. In both the Coomassie and western blot analysis, rHIFα migrated further into the gel than rHIFγ$_{(C387S)}$ even though rHIFγ$_{(C387S)}$ has a lower molecular weight, likely due to structural differences between the two proteins. Both expression plasmids were verified via DNA sequencing prior to these expression studies.

ImageJ analysis of the Coomassie-stained gel indicates that the proteins are at least 70% pure. Western blot analysis indicates the majority of the protein is expressed as the full-length protein.

Mechanical and Structural Analysis of rHIF Fibers

Figure 4:
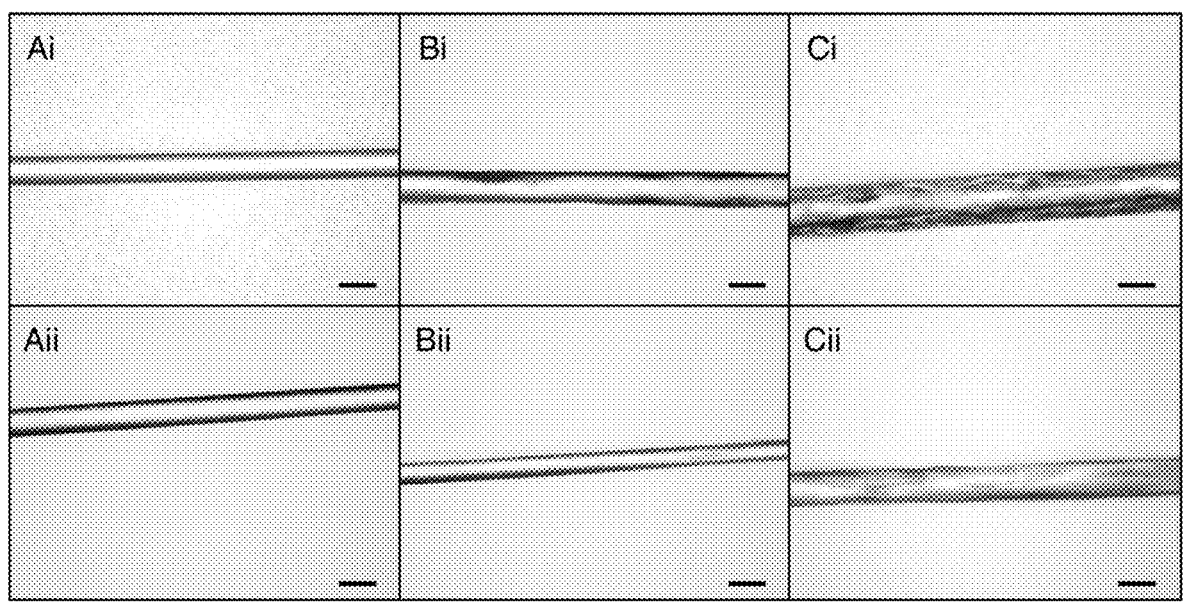
FIG. 4 provides light microscopy images of fiber at 400× magnification. (A) rHIFα fibers, (i) 1×1× stretch, and (ii) 2×2× stretch; (B) 1:1 rHIFα:rHIFγ$_{(C387S)}$ fibers, (i) 1×1× stretch, and (ii) 1.5×1.5× stretch; (C) rHIFγ$_{(C387S)}$ fibers, (i) 1×1× stretch, and (ii) 1.5×1.5× stretch. Scale bars are 25 μm.

All proteins and combinations readily spun fibers from HFIP using IPA as the coagulant solution. Images of the fibers using light microscopy at 400× magnification are presented in FIG. 4. As can be seen, fibers from rHIFα and the 1:1 combination fibers were generally smoother with less rough surface features than rHIFγ$_{(C387S)}$. However, most of the fibers generally appear smooth on the surface and have a reasonably well-defined circular shape. The fiber images in the bottom row of FIG. 4 correspond to the stretch at which that protein, or combination, had the highest tensile strength. Fiber images in the top row are all at 1×1× for comparison.

Figure 5:
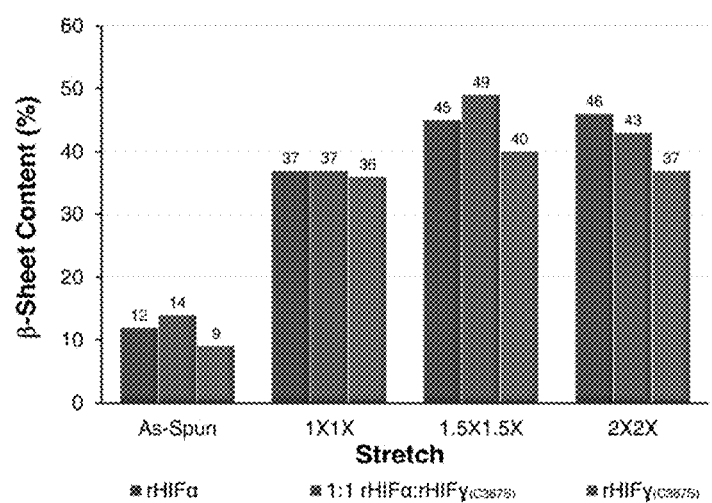
FIG. 5 is a graph depicting beta-sheet contents of various recombinant hagfish intermediate filament fibers as disclosed herein.
Figure 6:
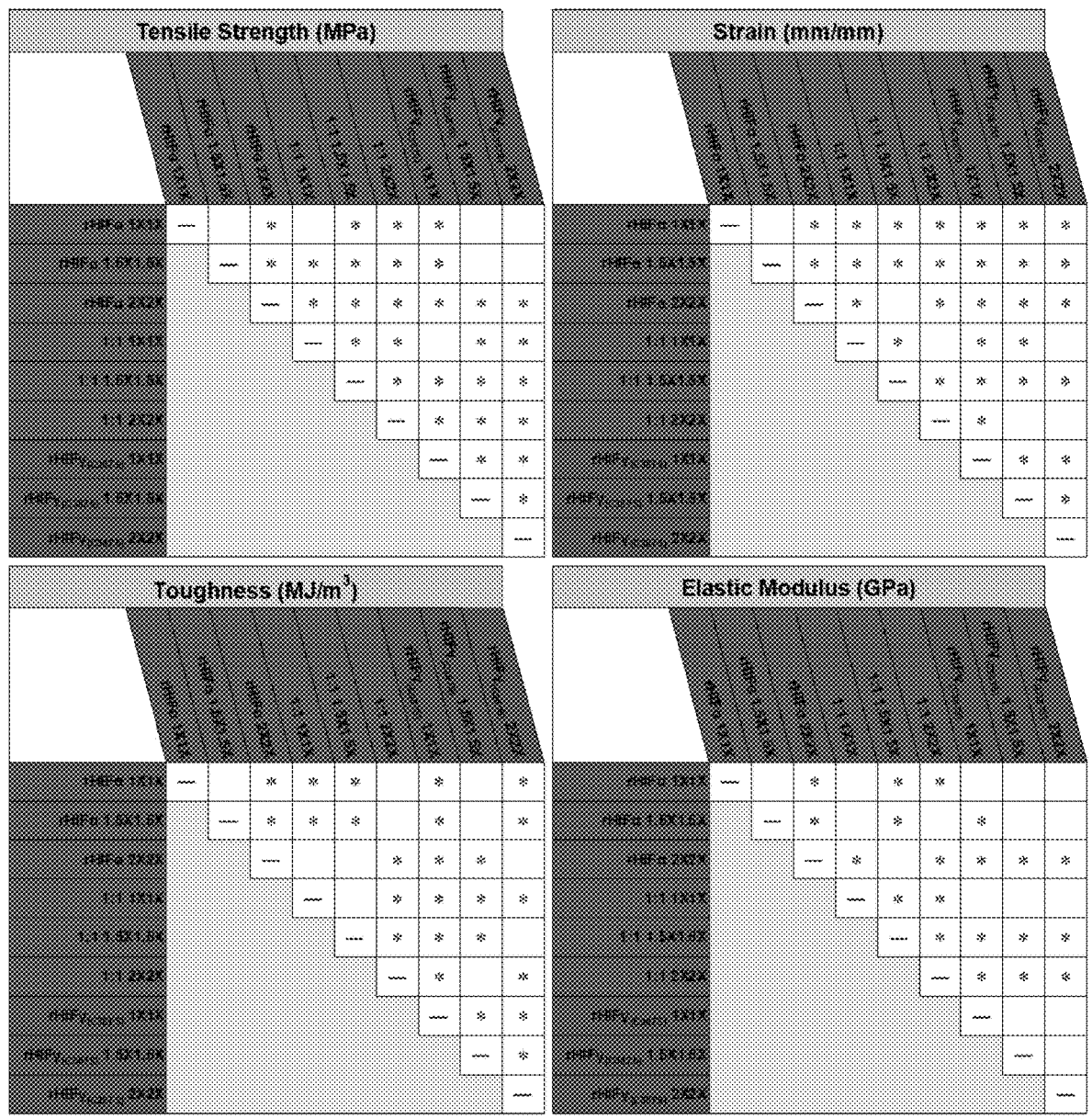
FIG. 6 is a series of tables disclosing mechanical characteristics of various recombinant hagfish intermediate filament fibers as disclosed herein.

The mechanical properties of the resulting fibers from this study exhibited substantial tensile strength, strain, toughness, and elastic modulus (Table 2). Between the homopolymeric fibers, rHIFα fibers demonstrated better mechanical properties than rHIFγ$_{(C387S)}$. As shown in Table 2 and FIG. 6, rHIFα did not have any significant changes in the characterized mechanical properties between 1×1× and 1.5× 1.5×. There was, however, an 8% increase in β-sheet content with the additional stretching (Table 2 and FIG. 5). At both stretches, rHIFα displayed the highest recorded strains at 0.92 and 0.87 mm/mm, and appreciable tensile strength at 104 and 106 MPa, respectively. This combination of the highest strains and higher strengths resulted in the rHIFα fibers having the highest toughness of all fibers tested with average values at 72 and 73 MJ/m$^3$, for 1×1× and 1.5×1.5×, respectively. Substantial decreases in fiber diameter and significant changes for all mechanical properties (FIG. 6) were observed at the 2×2× stretch without additional β-sheet recruitment. The fiber diameter decreased nearly 30% (16.7 μm), tensile stress increased 60% (169 MPa), strain decreased by 73% (0.23 mm/mm), toughness decreased by 55% (33 MJ/m$^3$), and the elastic modulus improved by 49% (5.4 GPa). It is notable that while having one of the highest tensile strengths and elastic modulus, the reduction in strain resulted in these fibers having the third lowest average toughness of all fibers. When these mechanical properties and the fiber diameter are compared to the 1:1 rHIFα: rHIFγ$_{(C387S)}$ combination fibers, at 1.5×1.5×, it is evident that the mechanical properties of rHIFα are remarkably similar with only the tensile strength being statistically significantly different (FIG. 6).

The 1×1× stretch factor for the 1:1 rHIFα:rHIFγ(C387S) combination fibers produced fibers that were not as robust as the rHIFα fibers but were mechanically superior to the rHIFγ$_{(C387S)}$ fibers. In fact, the mechanical properties of the 1:1 combination fibers almost fell perfectly between the values of the rHIFα and the rHIFγ$_{(C387S)}$ samples (Table 2). The 1:1 combination fibers at the 1.5×1.5× stretch demonstrated the highest tensile strength (199 MPa), the smallest fiber diameter (16.22 (μm), the lowest strain (0.21 mm/mm), and the highest elastic modulus (5.7 GPa) as well as the highest β-sheet content (49%) of all characterized fibers (FIG. 5). The 1.5×1.5× stretch appears to be optimal for obtaining maximum tensile stress and elastic modulus for this particular protein formulation. However, the lower strain resulted in a lower toughness (35 MJ/m$^3$). Interestingly, when the 1:1 combination fibers were stretched at 2×2×, there were significant differences across all mechanical properties (FIG. 6). The tensile strength decreased by 29% (149 MPa), the strain more than doubled (0.56 mm/mm), which nearly doubled the average toughness (66 MJ/m$^3$), and the elastic modulus was also 33% lower (4.1 MPa). Yet even with those reductions, this combination resulted in the third highest tensile strength of all the fiber combinations, demonstrating a relatively high degree of tunability through manipulations of draw-processing.

TABLE 4

Mechanical properties and structural composition results of spun rHIF fibers.

| Protein(s) | n | Diameter (μm) | Tensile Strength (MPa) | Strain (mm mm$^{-1}$) | Toughness (MJ m$^{-3}$) | Elastic Modulus (GPa) | β-Sheets (%) | α-Helices/ Random Coils/ Turns (%) |
|---|---|---|---|---|---|---|---|---|
| *As-Spun* | | | | | | | | |
| rHIFα | — | — | — | — | — | — | 12 | 88 |
| 1:1 rHIFα:rHIFγ$_{(C387S)}$ | — | — | — | — | — | — | 14 | 86 |
| rHIFγ$_{(C387S)}$ | — | — | — | — | — | — | 9 | 91 |
| *1X1X* | | | | | | | | |
| rHIFα | 20 | 23.4 ± 2.2 | 104 ± 22 | 0.92 ± 3.31 | 72 ± 22 | 3.4 ± 0.7 | 37 | 63 |
| 1:1 rHIFα:rHIFγ$_{(C387S)}$ | 20 | 25.7 ± 1.3 | 84 ± 11 | 0.42 ± 0.26 | 28 ± 17 | 3.2 ± 0.5 | 37 | 63 |
| rHIFγ$_{(C387S)}$ | 25 | 36.4 ± 8.3 | 74 ± 14 | 0.04 ± 0.01 | 1.8 ± 0.6 | 3 ± 0.5 | 36 | 64 |
| *1.5X1.5X* | | | | | | | | |
| rHIFα | 23 | 23.8 ± 0.6 | 106 ± 15 | 0.87 ± 0.18 | 73 ± 22 | 3.6 ± 0.3 | 45 | 55 |
| 1:1 rHIFα:rHIFγ$_{(C387S)}$ | 25 | 16.2 ± 0.8 | 199 ± 24 | 0.21 ± 0.07 | 35 ± 14 | 5.7 ± 0.9 | 49 | 51 |
| rHIFγ$_{(C387S)}$ | 25 | 20.2 ± 1.4 | 122 ± 23 | 0.62 ± 0.11 | 61 ± 13 | 3.5 ± 0.7 | 40 | 60 |
| *2X2X* | | | | | | | | |
| rHIFα | 23 | 16.8 ± 0.3 | 165 ± 17 | 0.23 ± 0.04 | 33 ± 7 | 5.4 ± 0.8 | 46 | 54 |
| 1:1 rHIFα:rHIFγ$_{(C387S)}$ | 25 | 17.7 ± 1.2 | 149 ± 26 | 0.56 ± 0.11 | 66 ± 18 | 4.1 ± 0.6 | 43 | 57 |
| rHIFγ$_{(C387S)}$ | 24 | 20.3 ± 3.0 | 120 ± 25 | 0.47 ± 0.10 | 43 ± 8 | 3.1 ± 0.6 | 37 | 63 |

The rHIFγ$_{(C387S)}$ fibers did not achieve a maximum value for any mechanical property. The 1×1× rHIFγ$_{(C387S)}$ consistently presented with the lowest mechanical properties for all of the characterized fibers (Table 4). rHIFγ$_{(C387S)}$ fibers performed well when stretched at around 1.5×1.5×, as the fiber diameter decreased by 57% (20.2 μm) and the highest tensile strength and strain of all rHIFγ$_{(C387S)}$ fibers (122 MPa and 0.62 mm/mm) were obtained, which resulted in an appreciable toughness (61 MJ/m$^3$). Additional stretching to 2×2× resulted in the reduction of all measured mechanical properties with significant decreases occurring for all properties with the exception of the elastic modulus (FIG. 6). The β-sheet content for rHIFγ$_{(C387S)}$ fibers at 2×2× also decreased to nearly 1×1× stretch levels when draw-processed further. All rHIFγ$_{(C387S)}$ also consistently demonstrated the lowest β-sheet content (FIG. 5 and Table 4) and the most limited range of elastic modulus (3-3.5 GPa).

The 1:1 rHIFα:rHIFγ$_{(C387S)}$ combination and rHIFα fibers achieved the highest tensile strengths yet reported for recombinant forms of hagfish intermediate filaments without chemical cross-linking at 199 MPa and 169 MPa, respectively. A wide range of mechanical properties was achieved between the individual proteins and the 1:1 combination fibers, indicating a wide range of tunability. All fibers saw substantially increased β-sheet content from the as-spun to 1×1× (FIG. 5 and Table 4), which was simply a result of the fiber being threaded through the instrument and exposed to the stretch bath solutions. As-spun fibers ranged from 9-14% β-sheet content, and all fibers increased nearly identically to 36-37% at 1×1×. Even with this sizeable initial increase, further stretching resulted in additional β-sheet recruitment, although in smaller increments, which resulted in substantial improvements in mechanical properties. Particularly notable is that when the 1:1 combination fibers were optimally stretched at 1.5×1.5×, the β-sheet content rose above both rHIFα and rHIFγ$_{(C387S)}$, which did not happen at any other stretch, although this was observed for the as-spun fibers that had not been stretched. Additionally, the β-sheet content of both 1:1rHIFα:rHIFγ$_{(C387S)}$ combination and rHIFγ$_{(C387S)}$ fibers decreased when draw-processed to the 2×2× level, which correlates with the measured mechanical properties, whereas the β-sheet content and mechanical properties of rHIFα fibers generally increased at this level.

A previous report on recombinantly produced hagfish intermediate filament proteins α and γ only achieved yields of 0.01-0.02 g/L when using *E. coli* as a host. Using methodologies developed during this study, substantial improvements were made to the protein yields, which were increased by 325 to 1000-fold from previous reports. This efficient and scalable purification process also allowed for the production of rHIF fibers with the highest mechanical properties yet reported for recombinant hagfish intermediate filament proteins. Furthermore, these fibers were produced with conventional wet-spinning techniques, instead of the standard method for hagfish proteins of solution casting and drawing, which allowed for continuous fiber lengths to be produced and drawn-processed as desired. The key developments and emphasis of this study are placed on the high expression and recovery of the proteins from bioreactor production, the development of a scalable purification strategy, and the generation and characterization of fibers from rHIFα and rHIFγ$_{(C387S)}$ individually and in combination using HFIP as the solvent.

Both rHIFα and rHIFγ$_{(C387S)}$ were produced and recovered at a laboratory production scale at ≥45 g/kg cell mass (≥8 g/L). This process was then scaled to a relatively large 100 L bioreactor, where the proteins were again recovered at similarly high levels. This makes them very economical. A possible bottleneck to the production of recombinant spider silk proteins is a general inability to produce native-sized proteins, with all structural elements present, at a sustainable level that supports systematization into engineering applications. The two recombinant forms of hagfish intermediate filaments investigated in this study do not suffer from this same problem. Not only are they readily produced in *E. coli*, but they are also produced as largely full-length synthetic analogs of the native proteins. Additionally, as Table 3 demonstrates, the levels of expression and recovery surpass, by more than two-fold, any reports of other structural fiber-forming proteins when produced in E. coli.

TABLE 5

Comparative expressions/yields of recombinantly produced fiber forming proteins

| Protein | MW (kDa) | Prod. (g/L) | Ref. |
|---|---|---|---|
| rHIFα | 70 | 6.5-10 | This work |
| rHIFγ(C387S) | 66 | 6.7-10 | This work |
| (rec)EsTKα, (rec)EsTKγ | 66.7, 62.8 | 0.01-0.02 | Fu et al. Biomacromolecules 16(8): 2327-2339 (2015) |
| MaSp1 | 100.7, 284.9 | 0.5-2.7 | Xia et al. Proc. Nat. Acad. Sci. 107(32): 14059-14063 (2010) |
| ADF3, ADF4 | 11.9-59.3 | 0.01-0.36 | Huemmerich et al. Biochemistry 43(42): 13604-13612 (2004) |
| MaSp2 | 201.6 | 3.6 | Yang et al. Process Biochem. 51(4): 484-490 (2016) |
| Honey Bee Silk | ≈40 | 2.5 | Weisman et al. Biomaterials 31(9): 2695-2700 (2010) |

The purification process involves inclusion body purifications. The insolubility of both proteins, when expressed as inclusion bodies, allows the use of urea to remove more soluble contaminating proteins. While for this study the process was accomplished using batch centrifugation, inclusion body purifications can also be scaled with systems such as large volume filtration. Large volume filtration systems may allow for improvements in purity, additional processing steps, and, if necessary, for refolding of the proteins to occur in a controllable and efficient manner. Further refinements of the purification process will predictably reduce the overall yield as more impurities are removed. This study induced cultures at an $OD_{600}$ of ≈60, but contemplates increasing induction of cultures having greater cell density, and therefore the total mass produced, through the continued use of bioreactor media and feedstocks. There are several reports in the literature of E. coli in bioreactors achieving optical densities above 100. If cell density correlates in a linear manner with total protein production and recovery, then yields in excess of 13 g/L could be expected and purified with the developed procedures.

In the only other literature report on the spinning of synthetically produced hagfish intermediate filament proteins α and γ into fibers, the authors were able to achieve tensile strengths between 25-150 MPa when the fibers were draw-processed and dried. The study used highly purified proteins and a refolding process to attempt to create the natural coiled-coil structure. In addition to highly purified proteins, the fiber spinning process was performed completely by hand and utilized the solution casting and drawing procedure, which could only be performed with small volumes (~2 μL) of protein dope solutions. Finally, the fibers were also cross-linked with glutaraldehyde to take advantage of the lysine concentration of the two proteins, and those fibers presented tensile strengths up to 250 MPa with predictably very little strain. Although the fibers presented in this previous study are impressive, the system has several limitations, including the yields, assembly methods, and spinning process.

This study utilized HFIP as a solvent due to its high propensity to generate α-helical conformations in proteins. As demonstrated, HFIP can produce protein fibers that recapitulate the natural fiber mechanical properties from recombinant analogs of the proteins. When the proteins are forced out of solution in the coagulation bath, the proteins interact, possibly creating a native-like coiled-coil structure, leading to fiber formation. Since the two proteins and the 1:1 combination readily formed fibers and demonstrated a substantial proportion of α-helical and random structures in the as-spun fibers, the characteristic coiled-coil structure presumably formed to some extent, although this was not directly measured in this study. The conversion of α-helices to β-sheets was demonstrated by the substantial recruitment of β-sheet from as-spun to 1×1× (where no deliberate stretch is applied), which supports that the transition can occur even with little force applied to the fiber. The varying compositions of the stretch baths, and the observed changes, also suggest that this structural transition can be influenced by environmental conditions. Increased stretching, or draw-processing, was successful in the additional recruitment of β-sheets that strongly correlate with the impressive gains of the mechanical properties (Table 4).

The highest average tensile strength and elastic modulus values were obtained by the 1:1 rHIFα:rHIFγ$_{(C387S)}$ combination fibers indicating a synergistic effect of having both proteins present in this system (Table 4 and FIG. 5). The β-sheet content of the 1:1 combination fibers at the 1.5×1.5× stretch is particularly indicative of this synergistic effect. Here, the β-sheet content exceeded that of both rHIFα and rHIFγ$_{(C387S)}$ when spun individually (Table 4 and FIG. 5). At both 1×1× and 2×2× stretches, the 1:1 combination fibers were a blend of the β-sheet content of rHIFα and rHIFγ$_{(C387S)}$. This indicates that when fibers are draw-processed as described herein, more β-sheets can be recruited when both proteins are present than either protein can achieve individually and produce more optimal mechanical properties.

Notably though, the rHIFα fibers were nearly as impressive as the 1:1 combination fibers and exceeded the mechanical properties reported from the previous study. The rHIFα fibers demonstrated the broadest range of strain, nearly doubling in initial length for the 1×1× stretch. However, when stretched further to 2×2×, the tensile strength, elastic modulus, strain, and β-sheet content were similar to the best-performing fibers in this study; the 1:1 combination at 1.5×1.5×. Unlike the other two protein formulations studied in this investigation the β-sheet content of rHIFα fibers increased for all stretches, and did not drop at the highest stretch performed. This suggests that each protein may respond uniquely to any processing and tuning. Particularly indicative of the tunability observed for these proteins is that between the 1×1× fibers and the 2×2× fibers, rHIFα lost 70% strain and gained nearly 63% more tensile strength.

Mechanical properties for rHIFγ$_{(C387S)}$ fibers were lower than both rHIFα and the 1:1 rHIFα:rHIFγ$_{(C387S)}$ combination fibers. However, they are still impressive mechanically when compared to previously reported fibers. Again, the stretch factor of 1.5×1.5× for rHIFγ$_{(C387S)}$ fibers produced the best fibers for this protein formulation, with some properties exceeding the prior synthetic proteins and regenerated natural slime threads. These fibers were also generally larger in diameter with larger surface deformities than either rHIFα or the 1:1 combination fibers. Both of these factors likely played a role in the observed mechanical properties.

Although not directly measured in this study, there is suggestive evidence that by stretching the fibers the β-sheets are being oriented along the axis of stretch through draw-processing. In particular, for the rHIFα fibers, at the 1.5× 1.5× stretch, the diameters averaged ~24 μm with 45% β-sheet content. When stretched to 2×2×, the diameters of the fibers dropped to ~17 μm, and the β-sheet content increased a negligible amount (45% to 46%), yet the fibers demonstrated a 63% increase in tensile strength and a 40% improvement in elastic modulus. It is unlikely that the large improvements were the result of a 1% increase in β-sheet content. A more plausible explanation is that the β-sheet crystallites became orientated along the axial stretch (the length of the fiber), which resulted in improvements in tensile strength, elastic modulus, and the reduction in fiber diameter.

For this study, only the individual proteins and their natural 1:1 combination were explored. However, the stark differences between the mechanical properties of the two proteins are intriguing as homopolymeric fibers. Varying the ratio beyond the natural 1:1 ratio will likely allow for the production of fibers with extensive tunability. For instance, producing a fiber with a high ratio of rHIFγ$_{(C387S)}$ would likely provide a less rigid fiber (lower elastic modulus) while the presence of rHIFα would improve the tensile strength of the fiber due to its increased ability to form β-sheets. The ratio of the two proteins could be tuned along with the post-spin draw to produce a fiber that exactly meets a mechanical requirement.

While this study indicates that these two proteins can be expressed at high levels in $E.\ coli$, the natural properties of hagfish intermediate filaments were not fully reproduced, although the highest mechanical properties were recorded to date. It is clear that the fiber diameter has a substantial contribution to the lower mechanical properties observed. Natural hagfish fibers, when isolated from the slime and dried, are reported at 1.27 μm, and when stretched and dried, the diameter decreases to 1.07 μm. The finest fibers produced from this study were 15 times larger in diameter than their natural counterparts. Reduction in the diameter and thus the cross-sectional area of the fibers, even by relatively small increments, may alter the mechanical properties. Supporting this, as indicated in Table 4, is that as the fiber diameters are decreased through draw-processing, the tensile strength and elastic modulus increase similar to other protein-based fibers. Conversely, as the diameter and strain increase, even if only slightly, there is a corresponding decrease in elastic modulus and tensile strength. Further refinements in the spinning process, such as alternative solvation methods, finer diameter needles, increased post-spin draw, alternative coagulation, and bath solutions, should result in the ability to obtain finer fibers with more native-like mechanical properties. Alternative spinning techniques that produce very fine fibers, such as electrospinning, are contemplated by this disclosure.

Hagfish intermediate filaments have tensile strengths that are near that of spider silk when dried and stretched. The hagfish intermediate filament protein molecular weights are much smaller than spider silks, and the overall amino acid distribution is also far less repetitive, which makes them a more amenable target for heterologous expression. Reported here is the markedly high production (~8 g/L) of the hagfish intermediate filament proteins, denoted α and γ, in $E.\ coli$ using efficient bioreactors that resulted in yields orders of magnitude higher (325-1000×) than previous reports on these two proteins. An efficient and scalable purification method was developed that allowed for the recovery of the proteins with high enough purities for the production of fibers. Hexafluoroisopropanol was used as a solvent from which to spin fibers. In this report, the two proteins were spun into fibers individually and also in their native 1:1 combination. The hallmark α-helix to β-sheet conversion was observed, which improved the mechanical performance. The 1:1 combination fibers had the highest mechanical properties yet reported, without the use of chemical cross-linking methods, with an average tensile strength of nearly 200 MPa and an elastic modulus of 5.7 GPa. However, the recombinant form of hagfish α performed nearly the same as the 1:1 combination fibers. The results suggest that varying the ratios of the two proteins beyond the 1:1 ratio found in nature will allow a degree of tunability to the mechanical properties and the performance of the fibers. This research demonstrates markedly high heterologous production of hagfish intermediate filament proteins in $E.\ coli$ with subsequent impressive mechanical properties of fibers spun from this system.

This work has demonstrated that the production of recombinant hagfish intermediate filament proteins, using $E.\ coli$ as a heterologous host, occurs at high enough levels to be commercially favorable. Furthermore, initial scale-up of the production system did not result in any significant reductions in the expression of the recombinant proteins. An effective purification strategy was also developed for the recovery of the rHIF proteins and resulted in yields that far surpassed other similarly produced fibrous structural proteins. The large quantities of recovered protein allowed for numerous, and rapid, progress to investigate fiber production methods, and ultimately resulted in noteworthy fibers. The fibers spun from these efforts bore some of the highest yet reported mechanical properties for these recombinantly produced forms of hagfish intermediate filament proteins. In addition to the high production yields and appreciable fiber properties, recombinant production also allowed the opportunity to study these proteins in non-mimetic states that do not occur naturally to better understand the individual functions and roles of these proteins. Through these individual and combined studies of the proteins and their fibers, it was determined that a broad range of tunability is possible for the mechanical properties of these synthetic fibers, which can be characteristically controlled by the proteins utilized, the protein structures, the processing methods, and possibly other unexplored factors. This study provides the first evidence that recombinant hagfish intermediate filament proteins can be produced at high enough levels to be a viable source of material for high-performance fibrous protein materials, while also providing a reasonable starting point for future investigations of these proteins or similar systems.

What is claimed is:

1. A recombinant hagfish intermediate filament gamma (HIFγ) protein of SEQ ID NO: 3.

2. An isolated or purified polynucleotide sequence encoding the recombinant hagfish intermediate filament protein of claim 1.

3. A vector comprising the polynucleotide sequence of claim 2.

4. A fiber comprising the recombinant hagfish intermediate filament protein of claim 1.

5. The fiber of claim 4, wherein the fiber further comprises hagfish intermediate filament alpha (HIFα) protein.

6. The fiber of claim 4, wherein the ratio of HIFα to HIFγ is about 10:1 to about 1:10.

7. The fiber of claim 4, having a diameter of about 15 microns to about 45 microns, having a tensile strength of about 150 megapascals to about 225 megapascals, having a toughness of about 50 megajoules per cubic meter to about 100 megajoules per cubic meter, having a strain of about 0.50 millimeter per millimeter to about 1.25 millimeter per millimeter, having an elastic modulus of about 3.5 gigapascals to about 7 gigapascals, or having a beta sheet content of about 35% to about 50%.

\* \* \* \* \*